(12) United States Patent
Medoff et al.

(10) Patent No.: US 9,428,621 B2
(45) Date of Patent: *Aug. 30, 2016

(54) PROCESSING BIOMASS

(71) Applicant: XYLECO, INC., Woburn, MA (US)

(72) Inventors: Marshall Medoff, Brookline, MA (US); Thomas Craig Masterman, Rockport, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/495,995

(22) Filed: Sep. 25, 2014

(65) Prior Publication Data

US 2015/0010989 A1 Jan. 8, 2015

Related U.S. Application Data

(63) Continuation of application No. 12/639,289, filed on Dec. 16, 2009, now Pat. No. 8,951,778.

(60) Provisional application No. 61/139,473, filed on Dec. 19, 2008.

(51) Int. Cl.
| | |
|---|---|
| *C08B 15/00* | (2006.01) |
| *C08H 8/00* | (2010.01) |
| *C08L 97/02* | (2006.01) |
| *C12P 7/10* | (2006.01) |
| *C12P 19/04* | (2006.01) |
| *C12P 7/16* | (2006.01) |
| *D21C 9/00* | (2006.01) |

(52) U.S. Cl.
CPC .... *C08H 8/00* (2013.01); *C08B 15/00* (2013.01); *C08L 97/02* (2013.01); *C12P 7/10* (2013.01); *C12P 7/16* (2013.01); *C12P 19/04* (2013.01); *C12P 2201/00* (2013.01); *D21C 9/001* (2013.01); *Y02E 50/16* (2013.01); *Y02E 50/32* (2013.01)

(58) Field of Classification Search
CPC ........................ D21C 9/001; C12P 2201/00
See application file for complete search history.

(56) References Cited

U.S. PATENT DOCUMENTS

| | | | |
|---|---|---|---|
| 3,883,413 | A | 5/1975 | Douglas-Hamilton |
| 4,314,854 | A | 2/1982 | Takagi |
| 4,769,082 | A | 9/1988 | Kumakura et al. |
| 6,046,375 | A | 4/2000 | Goodell et al. |

(Continued)

FOREIGN PATENT DOCUMENTS

| | | |
|---|---|---|
| CA | 2847243 | 6/2008 |
| DE | 222887 | 5/1985 |

(Continued)

OTHER PUBLICATIONS

Zhang et al., "Degradation of Calcium Lignosulfonate Using Gamma-Ray Irradiation", Chemospere, 2004, vol. 57, pp. 1181-1187.

(Continued)

*Primary Examiner* — Jonathan Hurst
(74) *Attorney, Agent, or Firm* — Leber Patent Law P.C.

(57) ABSTRACT

Biomass (e.g., plant biomass, animal biomass, and municipal waste biomass) is processed to produce useful products, such as fuels. For example, systems are described that can use feedstock materials, such as cellulosic and/or lignocellulosic materials and/or starchy materials, to produce ethanol and/or butanol, e.g., by fermentation.

18 Claims, 10 Drawing Sheets

(56) References Cited

U.S. PATENT DOCUMENTS

| | | |
|---|---|---|
| 7,396,974 B2 | 7/2008 | Goodell et al. |
| 2007/0178569 A1 | 8/2007 | Leschine et al. |

FOREIGN PATENT DOCUMENTS

| | | |
|---|---|---|
| DE | 271078 | 8/1989 |
| EP | 2111959 | 10/2009 |
| JP | 35-14554 | 10/1935 |
| JP | 56-127601 | 10/1981 |
| JP | 61-078390 | 4/1986 |
| JP | 07243184 | 9/1995 |
| JP | 2005-161134 | 6/2005 |
| JP | 2007-020555 | 2/2007 |
| JP | 2008-006372 | 1/2008 |
| WO | 2006119392 | 11/2006 |
| WO | 2007001229 | 1/2007 |
| WO | 2008073186 | 6/2008 |
| WO | 2009125190 | 10/2009 |
| WO | 2010080428 | 7/2010 |

OTHER PUBLICATIONS

Bentivenga et al., "Degradation of Steam-Exploded Lignin from Beech by Using Fenton's Reagent", Biomass and Bioenergy, vol. 24, 2002, pp. 233-238.

Varela, "Effect of pH and Oxalate on Hydroquinone-Derived Hydroxyl Radical Formation during Brown Rot Wood Degradation", Applied and Environmental Microbiology, vol. 70, No. 1, 2004, pp. 324-331.

Wang et al., "Analysis of Pretreatment Methods in Ethanol Production Process with Straw", J. Anhui Agric. Sci., vol. 35:6883-6, 2007 (Chinese).

Chunyan et al., "Influence of Biological Pretreatment on Saccharification of Bamboo with Cellulase", Scientia Silvae Sinicae, vol. 44:168-72, 2008 (Chinese).

Han, Y.W., "Gamma-Ray-Induced Degradation of Lignocellulosic Materials", Biotechnology and Bioengineering, vol. XXIII, 1981, p. 2525-2535.

Detroy et al., "Biomass Conversion: Fermentation Chemical and Fuels", CRC Critical Reviews in Microbiology, vol. 10, Issue 3, 1983, pp. 203-228.

Bono et al., "Pretreatment of Poplar Lignocellulose by Gamma-Ray or Ozone for Subsequent Fungal Biodegradation", Applied Microbiology and Biotechnology, vol. 22, 1985, pp. 227-234.

Ershov, "Radiation-Chemical Degradation of Cellulose and Other Polysaccarides", Russian Chemical Reviews, vol. 67 (4), 1998, pp. 315-334.

Kerr, T.J. et al., "Chemical Composition and In-Vitro Digestibility of Biologically Degraded Peanut Hulls", Journal of the Science of Food and Agriculture, Wiley & Sons, Chichester, GB, vol. 37, No. 7, Jan. 1, 1986, pp. 637-651.

Anderson et al., "Structural and Chemical Properties of Grass Lignocelluloses Related to Conversion for Biofuels", Journal of Industrial Microbiology & Biotechnology: Official Journal of the Society for Industrial Microbiology, Springer, Berlin, DE, vol. 35, No. 5, Jan. 8, 2008, pp. 355-366.

Riquelme-Valdes et al., "Fiberboard Manufactured Without Resin Using the Fenton Reaction", Chilean Chemical Society Journal, Sociedad Chilena de Quimica, Paicavi, CL, vol. 53, No. 4, Jan. 1, 2008, pp. 1722-1725.

Schilling et al., "Synergy between Pretreatment Lignocellulose Modifications and Saccharification Efficiency in Two Brown Rot Fungal Systems", Applied Microbiology and Biotechnology, Springer Verlag, Berlin, DE, vol. 84, No. 3, Sep. 1, 2009, pp. 465-475.

Dashtban et al., "Fungal Bioconversion of Lignocellulosic Residues: Opportunities and Perspectives", International Journal of Biological Sciences, vol. 5, No. 6, Sep. 4, 2009, pp. 578-595.

ISR and Written Opinion for PCT/US2009/068202, Mar. 31, 2010, 11 pages.

Cohen, R. et al., "Differential Stress-Induced Regulation of Two Quinone Reductases in the Brown Rot Basidiomycete Gloeophyllum trabeum", Applied and Environmental Microbiology, vol. 70, No. 1, Jan. 2004, pp. 324-331.

Singapore Search Report, Singapore Application No. 2013017314, dated May 19, 2015, 8 pages.

Office Action, Corresponding Japanese Patent Application No. 2015-063580, dated Jul. 23, 2015, 4 pages.

Pre-Trial Report, Corresponding Japanese Application No. 2011-542368, dated Jul. 21, 2015, 4 pages.

PROCESSING BIOMASS

RELATED APPLICATIONS

This application is a continuation application of U.S. application Ser. No. 12/639,289, now U.S. Pat. No. 8,951,778, filed Dec. 16, 2009, which claims priority to U.S. Provisional Application Ser. No. 61/139,473 filed Dec. 19, 2008. The complete disclosures of each such application are hereby incorporated by reference herein.

BACKGROUND

Various carbohydrates, such as cellulosic and lignocellulosic materials, e.g., in fibrous form, are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described, for example, in U.S. Pat. Nos. 7,307,108, 7,074,918, 6,448,307, 6,258,876, 6,207,729, 5,973,035 and 5,952,105.

SUMMARY

Generally, this invention relates to carbohydrate-containing materials (e.g., biomass materials or biomass-derived materials, such as starchy materials and/or cellulosic or lignocellulosic materials), methods of making and processing such materials to change their structure and/or their recalcitrance level, and products made from the changed materials. For example, many of the methods described herein can provide cellulosic and/or lignocellulosic materials that have an oxygen-rich functionality, a lower molecular weight and/or crystallinity relative to a native material. Many of the methods, such as Fenton oxidation methods, provide materials that can be more readily utilized by a variety of microorganisms (with or without enzymatic hydrolysis) to produce useful products, such as hydrogen, alcohols (e.g., ethanol or butanol), organic acids (e.g., acetic acid), hydrocarbons, co-products (e.g., proteins) or mixtures of any of these. Many of the products obtained, such as ethanol or n-butanol, can be utilized as fuel, e.g., as an internal combustion fuel or as a fuel cell feedstock. In addition, the products described herein can be utilized for electrical power generation, e.g., in a conventional steam generating plant or in a fuel cell plant.

In one aspect, the invention features methods of changing molecular structures and/or reducing recalcitrance in materials, such as hydrocarbon-containing materials and/or biomass materials, e.g., cellulosic or lignocellulosic materials, such as any one or more unprocessed (e.g., cut grass), semi-processed (e.g., comminuted grass) or processed materials (e.g., comminuted and irradiated grass) described herein.

The methods can feature oxidative methods of reducing recalcitrance in cellulosic or lignocellulosic materials that employ Fenton-type chemistry. Fenton-type chemistry is discussed in Pestovsky et al., Angew. Chem., Int. Ed. 2005, 44, 6871-6874, the entire disclosure of which is hereby incorporated by reference herein. The methods can also feature combinations of Fenton oxidation and any other pretreatment method described herein in any order.

Without wishing to be bound by any particular theory, it is believed that oxidation increases the number of hydrogen-bonding groups on the cellulose and/or the lignin, such as hydroxyl groups, aldehyde groups, ketone groups carboxylic acid groups or anhydride groups, which can increase its dispersability and/or its solubility.

In one aspect, the invention features methods that include contacting, in a mixture, a first cellulosic or lignocellulosic material having a first level of recalcitrance with one or more compounds comprising one or more naturally-occurring, non-radioactive metallic elements, e.g., non-radioactive group 5, 6, 7, 8, 9, 10 or 11 elements, and, optionally, one or more oxidants capable of increasing an oxidation state of at least some of said elements, to produce a second cellulosic or lignocellulosic material having a second level of recalcitrance lower than the first level of recalcitrance.

Other methods include combining a hydrocarbon-containing material with one or more compounds including one or more naturally-occurring, non-radioactive metallic elements, e.g., non-radioactive group 5, 6, 7, 8, 9, 10 or 11 elements to provide a mixture in which the one or more compounds contact the hydrocarbon-containing material; and maintaining the contact for a period of time and under conditions sufficient to change the structure of the hydrocarbon-containing material.

In some embodiments, the method further includes combining the first cellulosic, lignocellulosic, or hydrocarbon-containing material with one or more oxidants capable of increasing an oxidation state of at least some of the elements. In such instances, the one or more oxidants contact the material with the one or more compounds in the mixture. In some embodiments, the one or more oxidants include ozone and/or hydrogen peroxide.

In some embodiments, the one or more elements are in a 1+, 2+, 3+, 4+ or 5+ oxidation state. In particular instances, the one or more elements are in a 2+, 3+ or 4+ oxidation state. For example, iron can be in the form of iron(II), iron(III) or iron(IV).

In particular instances, the one or more elements include Mn, Fe, Co, Ni, Cu or Zn, preferably Fe or Co. For example, the Fe or Co can be in the form of a sulfate, e.g., iron(II) or iron(III) sulfate.

In some embodiments, the one or more oxidants are applied to the first cellulosic or lignocellulosic material and the one or more compounds as a gas, such as by generating ozone in-situ by irradiating the first cellulosic or lignocellulosic material and the one or more compounds through air with a beam of particles, such as electrons or protons.

In some embodiments, the mixture further includes one or more hydroquinones, such as 2,5-dimethoxyhydroquinone and/or one or more benzoquinones, such as 2,5-dimethoxy-1,4-benzoquinone. Such compounds, which have similar molecular entities as lignin, can aid in electron transfer.

In some desirable embodiments, the one or more oxidants are electrochemically or electromagnetically generated in-situ. For example, hydrogen peroxide and/or ozone can be electrochemically or electromagnetically produced within a contact or reaction vessel or outside the vessel and transferred into the vessel.

The methods may further include contacting the second cellulosic or lignocellulosic material with an enzyme and/or microorganism. Products produced by such contact can include any of those products described herein, such as food or fuel, e.g., ethanol, or any other products described in U.S. Provisional Application Ser. No. 61/139,453, which is hereby incorporated by reference herein in its entirety.

In another aspect, the invention features systems that include a structure or carrier, e.g., a reaction vessel, containing a mixture including 1) any material described herein, such as a cellulosic or lignocellulosic material and 2) one or more compounds comprising one or more naturally-occurring, non-radioactive metallic elements, e.g., non-radioactive group 5, 6, 7, 8, 9, 10 or 11 elements. Optionally, the mixture can include 3) one or more oxidants capable of increasing an oxidation state of at least some of the elements.

In another aspect, the invention features compositions that include 1) any material described herein, such as a cellulosic or lignocellulosic material and 2) one or more compounds comprising one or more naturally-occurring, non-radioactive group 5, 6, 7, 8, 9, 10 or 11 elements. Optionally, the composition can include one or more oxidants capable of increasing an oxidation state of at least some of the elements.

In another aspect, the invention features methods of changing molecular structures and/or reducing recalcitrance in biomass materials, such as cellulosic or lignocellulosic materials. The methods include combining a first lignocellulosic material having a first level of recalcitrance with one or more ligninases and/or one or more biomass-destroying, e.g., lignin-destroying organisms, in a manner that the one or more ligninases and/or organisms contact the first cellulosic or lignocellulosic material; and maintaining the contact for a period of time and under conditions sufficient to produce a second lignocellulosic material having a second level of recalcitrance lower than the first level of recalcitrance. The method can further include contacting the second cellulosic or lignocellulosic material with an enzyme and/or microorganism, e.g., to make any product described herein, e.g., food or fuel, e.g., ethanol or butanol (e.g., n-butanol) or any product described in U.S. Provisional Application Ser. No. 61/139,453.

The ligninase can be, e.g., one or more of manganese peroxidase, lignin peroxidase or laccases.

The biomass-destroying organism can be, e.g., one or more of white rot, brown rot or soft rot. For example, the biomass-destroying organism can be a Basidiomycetes fungus. In particular embodiments, the biomass-destroying organism is *Phanerochaete chrysoporium* or *Gleophyllum trabeum.*

In certain embodiments, the first material is in the form of a fibrous material that includes fibers provided by shearing a fiber source. Shearing alone can reduce the crystallinity of a fibrous material and can work synergistically with any process technique that also reduces crystallinity and/or molecular weight. For example, the shearing can be performed with a rotary knife cutter. In some embodiments, the fibrous material has an average length-to-diameter ratio of greater than 5/1.

The first and/or second material can have, e.g., a BET surface area of greater than 0.25 m$^2$/g and/or a porosity of greater than about 25 percent.

To further aid in the reduction of the molecular weight of the cellulose, an enzyme, e.g., a cellulolytic enzyme, or a chemical, e.g., sodium hypochlorite, an acid, a base or a swelling agent, can be utilized with any method described herein.

When a microorganism is utilized, it can be a natural microorganism or an engineered microorganism. For example, the microorganism can be a bacterium, e.g., a cellulolytic bacterium, a fungus, e.g., a yeast, an enzyme, a plant or a protist, e.g., an algae, a protozoa or a fungus-like protist, e.g., a slime mold. When the organisms are compatible, mixtures may be utilized. Generally, various microorganisms can produce a number of useful products, such as a fuel, by operating on, e.g., fermenting the materials. For example, alcohols, organic acids, hydrocarbons, hydrogen, proteins or mixtures of any of these materials can be produced by fermentation or other processes.

Examples of products that may be produced include mono- and polyfunctional C1-C6 alkyl alcohols, mono- and polyfunctional carboxylic acids, C1-C6 hydrocarbons, and combinations thereof. Specific examples of suitable alcohols include methanol, ethanol, propanol, isopropanol, butanol, ethylene glycol, propylene glycol, 1,4-butane diol, glycerin, and combinations thereof. Specific example of suitable carboxylic acids include formic acid, acetic acid, propionic acid, butyric acid, valeric acid, caproic acid, palmitic acid, stearic acid, oxalic acid, malonic acid, succinic acid, glutaric acid, oleic acid, linoleic acid, glycolic acid, lactic acid, γ-hydroxybutyric acid, and combinations thereof. Examples of suitable hydrocarbons include methane, ethane, propane, pentane, n-hexane, and combinations thereof. Many of these products may be used as fuels.

The term "fibrous material", as used herein, is a material that includes numerous loose, discrete and separable fibers. For example, a fibrous material can be prepared from a bleached Kraft paper fiber source by shearing, e.g., with a rotary knife cutter.

The term "screen", as used herein, means a member capable of sieving material according to size. Examples of screens include a perforated plate, cylinder or the like, or a wire mesh or cloth fabric.

The term "pyrolysis", as used herein, means to break bonds in a material by the application of heat energy. Pyrolysis can occur while the subject material is under vacuum, or immersed in a gaseous material, such as an oxidizing gas, e.g., air or oxygen, or a reducing gas, such as hydrogen.

Oxygen content is measured by elemental analysis by pyrolyzing a sample in a furnace operating at 1300° C. or above.

Examples of biomass feedstock include paper, paper products, paper waste, wood, wood wastes and residues, particle board, sawdust, agricultural waste and crop residues, sewage, silage, grasses, rice hulls, bagasse, cotton, jute, hemp, flax, bamboo, sisal, abaca, straw, corn cobs, corn stover, switchgrass, alfalfa, hay, rice hulls, coconut hair, cotton, synthetic celluloses, seaweed, algae, municipal waste, or mixtures of these. The biomass can be or can include a natural or a synthetic material.

The terms "plant biomass" and "lignocellulosic biomass" refer to virtually any plant-derived organic matter (woody or non-woody).

For the purposes of this disclosure, carbohydrates are materials that are composed entirely of one or more saccharide units or that include one or more saccharide units. Carbohydrates can be polymeric (e.g., equal to or greater than 10-mer, 100-mer, 1,000-mer, 10,000-mer, or 100,000-mer), oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different. Examples of polymeric carbohydrates include cellulose, xylan, pectin, and starch, while cellobiose and lactose are examples of dimeric carbohydrates. Examples of monomeric carbohydrates include glucose and xylose. Carbohydrates can be part of a supramolecular structure, e.g., covalently bonded into the structure. Examples of such materials include lignocellulosic materials, such as that found in wood.

A starchy material is one that is or includes significant amounts of starch or a starch derivative, such as greater than about 5 percent by weight starch or starch derivative. For purposes of this disclosure, a starch is a material that is or includes an amylose, an amylopectin, or a physical and/or chemical mixture thereof, e.g., a 20:80 or 30:70 percent by weight mixture of amylose to amylopectin. For example, rice, corn, and mixtures thereof are starchy materials. Starch derivatives include, e.g., maltodextrin, acid-modified starch, base-modified starch, bleached starch, oxidized starch, acetylated starch, acetylated and oxidized starch, phosphate-modified starch, genetically-modified starch and starch that is resistant to digestion.

Swelling agents as used herein are materials that cause a discernable swelling, e.g., a 2.5 percent increase in volume over an unswollen state of cellulosic and/or lignocellulosic materials, when applied to such materials as a solution, e.g., a water solution. Examples include alkaline substances, such as sodium hydroxide, potassium hydroxide, lithium hydroxide and ammonium hydroxides, acidifying agents, such as mineral acids (e.g., sulfuric acid, hydrochloric acid and phosphoric acid), salts, such as zinc chloride, calcium carbonate, sodium carbonate, benzyltrimethylammonium sulfate, and basic organic amines, such as ethylene diamine.

A "sheared material", as used herein, is a material that includes discrete fibers in which at least about 50% of the discrete fibers, have a length/diameter (L/D) ratio of at least about 5, and that has an uncompressed bulk density of less than about 0.6 g/cm$^3$. A sheared material is thus different from a material that has been cut, chopped or ground.

Changing a molecular structure of a biomass feedstock, as used herein, means to change the chemical bonding arrangement or conformation of the structure. For example, the change in the molecular structure can include changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or an changing an overall domain size.

Unless otherwise defined, all technical and scientific terms used herein have the same meaning as commonly understood by one of ordinary skill in the art to which this invention belongs. All publications, patent applications, patents, and other references mentioned herein or attached hereto are incorporated by reference in their entirety for all that they contain.

Any biomass material, e.g., carbohydrate-containing material, e.g., cellulosic and/or lignocellulosic material described herein can be utilized in any application or process described in any patent or patent application incorporated by reference herein.

Other features and advantages of the invention will be apparent from the following detailed description, and from the claims.

DETAILED DESCRIPTION

Figure 1:
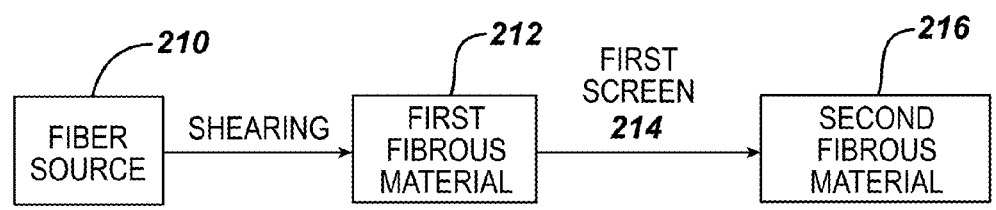
FIG. 1 is block diagram illustrating conversion of a fiber source into a first and second fibrous material.

Using the methods described herein, biomass can be processed to a lower level of recalcitrance and converted into useful products such as fuels. Systems and processes are described below that can use as feedstocks materials such as cellulosic and/or lignocellulosic materials that are readily available, but can be difficult to process, for example, by saccharification and/or by fermentation. In some implementations the feedstock materials are first physically prepared for processing, for example by size reduction. The physically prepared feedstock is then pretreated using oxidation (e.g., using Fenton-type chemistry), and may in some cases be further treated with one or more of radiation, sonication, pyrolysis, and steam explosion. Alternatively, in some cases, the feedstock is first treated with one or more of radiation, sonication, pyrolysis, and steam explosion, and then treated using oxidation, e.g., Fenton-type chemistry.

Preferred oxidative methods for reducing recalcitrance in cellulosic or lignocellulosic materials include Fenton-type chemistry, discussed above, in which one or more group 5, 6, 7, 8, 9, 10 or 11 elements, optionally along with one or more oxidants capable of increasing an oxidation state of at least some of the elements are utilized.

After pretreatment, the pretreated material can be further processed, e.g., using primary processes such as saccharification and/or fermentation, to produce a product.

Types of Biomass

Generally, any biomass material that is or includes carbohydrates composed entirely of one or more saccharide units or that include one or more saccharide units can be processed by any of the methods described herein. For example, the biomass material can be cellulosic or lignocellulosic materials, or starchy materials, such as kernels of corn, grains of rice or other foods.

Fiber sources include cellulosic fiber sources, including paper and paper products (e.g., polycoated paper and Kraft paper), and lignocellulosic fiber sources, including wood, and wood-related materials, e.g., particle board. Other suitable fiber sources include natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; and synthetic fiber sources, e.g., extruded yarn (oriented yarn or un-oriented yarn). Natural or synthetic fiber sources can be obtained from virgin scrap textile materials, e.g., remnants or they can be post consumer waste, e.g., rags. When paper products are used as fiber sources, they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Also, the fiber source can be obtained or derived from human (e.g., sewage), animal or plant wastes. Additional fiber sources have been described in U.S. Pat. Nos. 6,448,307, 6,258,876, 6,207,729, 5,973,035 and 5,952,105, the full disclosures of which are incorporated by reference herein.

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any one or more starchy material is also a starchy material. In particular embodiments, the starchy material is derived from corn. Various corn starches and derivatives are described in "Corn Starch", Corn Refiners Association (11$^{th}$ Edition, 2006), which is hereby incorporated by reference herein.

Blends of any biomass materials described herein can be utilized for making any of the products described herein, such as ethanol. For example, blends of cellulosic materials and starchy materials can be utilized for making any product described herein.

Feed Preparation

In some cases, methods of processing begin with a physical preparation of the feedstock, e.g., size reduction of raw feedstock materials, such as by cutting, grinding, shearing or chopping. In some cases, loose feedstock (e.g., recycled paper, starchy materials, or switchgrass) is prepared by shearing or shredding. Screens and/or magnets can be used to remove oversized or undesirable objects such as, for example, rocks or nails from the feed stream.

Feed preparation systems can be configured to produce feed streams with specific characteristics such as, for example, specific maximum sizes, specific length-to-width, or specific surface areas ratios. As a part of feed preparation, the bulk density of feedstocks can be controlled (e.g., increased). If desired, lignin can be removed from any feedstock that includes lignin.

Size Reduction

In some embodiments, the material to be processed is in the form of a fibrous material that includes fibers provided by shearing a fiber source. For example, the shearing can be performed with a rotary knife cutter.

For example, and by reference to FIG. 1, a fiber source 210 is sheared, e.g., in a rotary knife cutter, to provide a first fibrous material 212. The first fibrous material 212 is passed through a first screen 214 having an average opening size of 1.59 mm or less (1/16 inch, 0.0625 inch) to provide a second fibrous material 216. If desired, fiber source can be cut prior to the shearing, e.g., with a shredder.

In some embodiments, the shearing of fiber source and the passing of the resulting first fibrous material through first screen are performed concurrently. The shearing and the passing can also be performed in a batch-type process.

Figure 2:
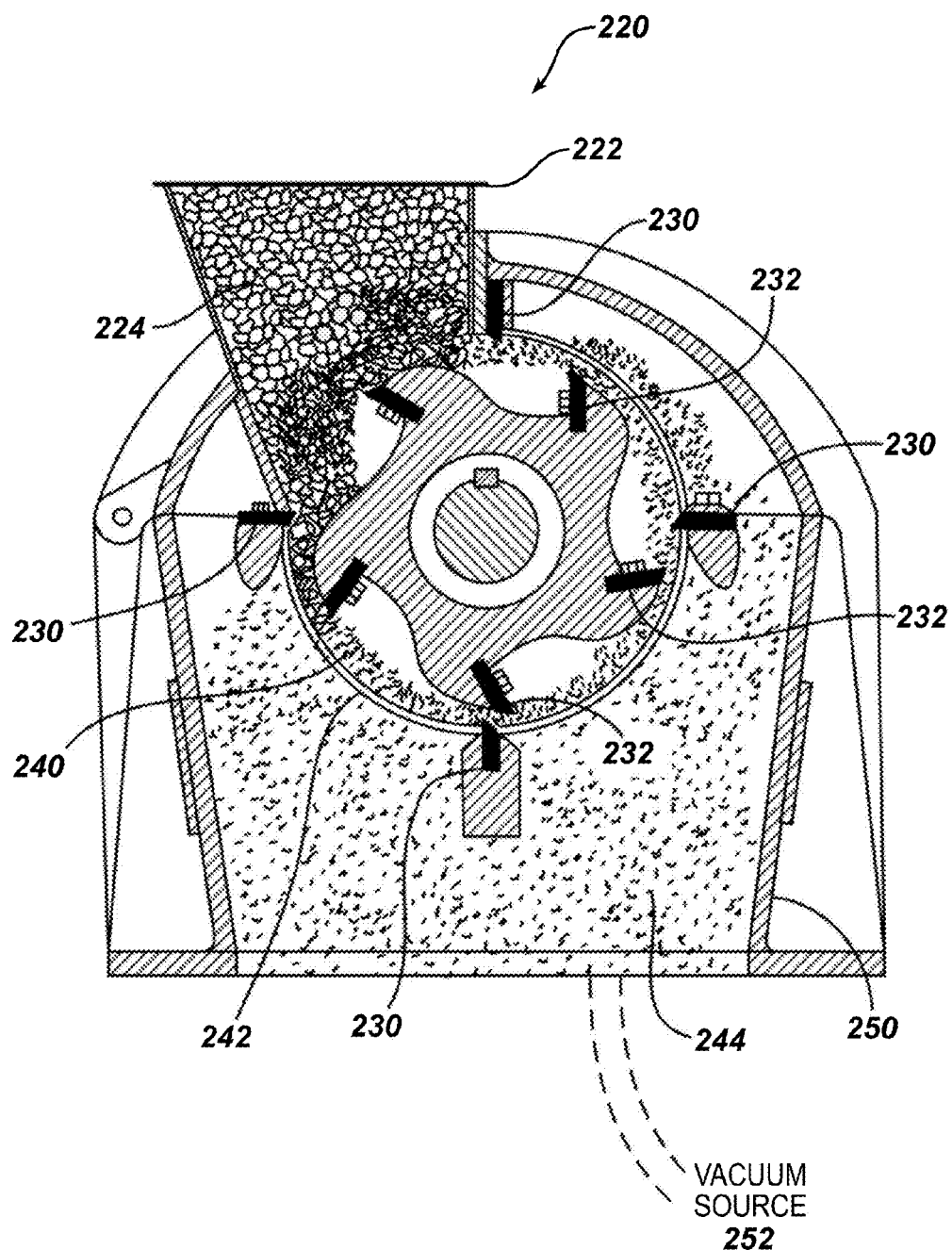
FIG. 2 is a cross-sectional view of a rotary knife cutter.

For example, a rotary knife cutter can be used to concurrently shear the fiber source and screen the first fibrous material. Other methods of making the fibrous materials include, e.g., stone grinding, mechanical ripping or tearing, pin grinding or air attrition milling. Referring to FIG. 2, a rotary knife cutter 220 includes a hopper 222 that can be loaded with a shredded fiber source 224. The shredded fiber source is sheared between stationary blades 230 and rotating blades 232 to provide a first fibrous material 240. First fibrous material 240 passes through screen 242, and the resulting second fibrous material 244 is captured in bin 250. To aid in the collection of the second fibrous material, a vacuum source 252 can be utilized to maintain the bin at a pressure below nominal atmospheric pressure, e.g., at least 10, 25, 50 or 75 percent below nominal atmospheric pressure.

Shearing can be advantageous for "opening up" and "stressing" the fibrous materials, making the cellulose of the materials more susceptible to chain scission and/or reduction of crystallinity. The open materials can also be more susceptible to oxidation.

The fiber source can be sheared in a dry state, a hydrated state (e.g., having up to ten percent by weight absorbed water), or in a wet state, e.g., having between about 10 percent and about 75 percent by weight water. The fiber source can even be sheared while partially or fully submerged under a liquid, such as water, ethanol, isopropanol. The fiber source can also be sheared under a gas (such as a stream or atmosphere of gas other than air), e.g., oxygen or nitrogen, or steam.

In some embodiments, the average opening size of the first screen 214 is less than 0.79 mm (0.031 inch), e.g., less than 0.51 mm (0.020 inch), 0.40 mm (0.015 inch), 0.23 mm (0.009 inch), 0.20 mm (0.008 inch), 0.18 mm (0.007 inch), 0.13 mm (0.005 inch), or even less than less than 0.10 mm (0.004 inch). The characteristics of suitable screens are described, for example, in US 2008-0206541. In some embodiments, the open area of the mesh is less than 52%, e.g., less than 41%, less than 36%, less than 31%, or less than 30%.

Figure 3:
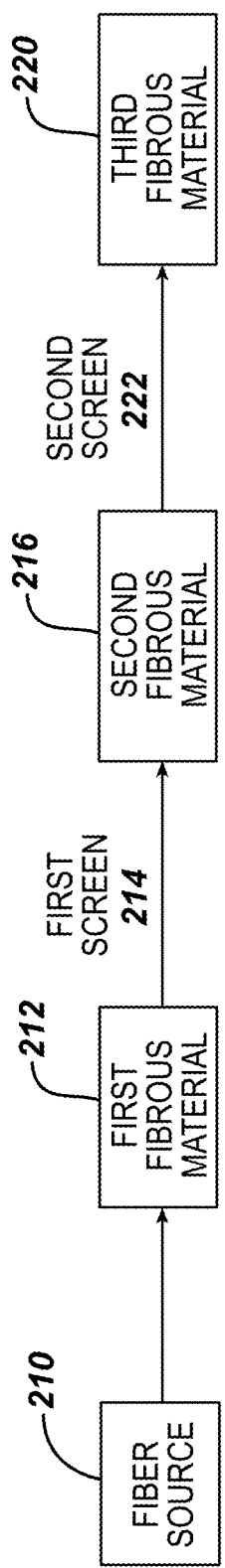
FIG. 3 is block diagram illustrating conversion of a fiber source into a first, second and third fibrous material.

In some embodiments, the second fibrous is sheared and passed through the first screen, or a different sized screen. In some embodiments, the second fibrous material is passed through a second screen having an average opening size equal to or less than that of first screen. Referring to FIG. 3, a third fibrous material 220 can be prepared from the second fibrous material 216 by shearing the second fibrous material 216 and passing the resulting material through a second screen 222 having an average opening size less than the first screen 214. In such instances, a ratio of the average length-to-diameter ratio of the second fibrous material to the average length-to-diameter ratio of the third fibrous material can be, e.g., less than 1.5, e.g., less than 1.4, less than 1.25, or even less than 1.1.

Generally, the fibers of the fibrous materials can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (i.e., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

The average length-to-diameter ratio of the second fibrous material 14 can be, e.g. greater than 8/1, e.g., greater than 10/1, greater than 15/1, greater than 20/1, greater than 25/1, or greater than 50/1. An average length of the second fibrous material 14 can be, e.g., between about 0.5 mm and 2.5 mm, e.g., between about 0.75 mm and 1.0 mm, and an average width (i.e., diameter) of the second fibrous material 14 can be, e.g., between about 5 µm and 50 µm, e.g., between about 10 µm and 30 µm.

In some embodiments, a standard deviation of the length of the second fibrous material 14 is less than 60 percent of an average length of the second fibrous material 14, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the second fibrous material is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$.

A porosity of the second fibrous material 14 can be, e.g., greater than 20, 25, 35, 50, 60, 70, 80, 85, 90, 92, 94, 95, 97.5 or 99 percent, or even greater than 99.5 percent.

In some embodiments, a ratio of the average length-to-diameter ratio of the first fibrous material to the average length-to-diameter ratio of the second fibrous material is, e.g., less than 1.5, e.g., less than 1.4, less than 1.25, less than 1.1, less than 1.075, less than 1.05, less than 1.025, or even substantially equal to 1.

In some embodiments, the third fibrous material is passed through a third screen to produce a fourth fibrous material. The fourth fibrous material can be, e.g., passed through a fourth screen to produce a fifth material. Similar screening processes can be repeated as many times as desired to produce the desired fibrous material having the desired properties.

In some implementations, the size reduction equipment may be portable, e.g., in the manner of the mobile processing equipment described in U.S. Provisional Patent Application Ser. No. 60/832,735, now Published International Application No. WO 2008/011598.

Pretreatment

Physically prepared feedstock can be pretreated for use in primary production processes such as saccharification and fermentation by, for example, reducing the average molecular weight and crystallinity of the feedstock and/or increasing the surface area and/or porosity of the feedstock. Pretreatment processes include utilizing Fenton-type chemistry, discussed above, and can further include one or more of irradiation, sonication, oxidation, pyrolysis, and steam explosion.

Fenton Chemistry

In some embodiments, the one or more elements used in the Fenton reaction are in a 1+, 2+, 3+, 4+ or 5+ oxidation state. In particular instances, the one or more elements include Mn, Fe, Co, Ni, Cu or Zn, preferably Fe or Co. For example, the Fe or Co can be in the form of a sulfate, e.g., iron(II) or iron(III) sulfate. In particular instances, the one or more elements are in a 2+, 3+ or 4+ oxidation state. For example, iron can be in the form of iron(II), iron(III) or iron(IV).

Exemplary iron (II) compounds include ferrous sulfate heptahydrate, iron(II) acetylacetonate, (+)-iron(II) L-ascorbate, iron(II) bromide, iron(II) chloride, iron(II) chloride hydrate, iron(II) chloride tetrahydrate, iron(II) ethylenediammonium sulfate tetrahydrate, iron(II) fluoride, iron(II) gluconate hydrate, iron(II) D-gluconate dehydrate, iron(II) iodide, iron(II) lactate hydrate, iron(II) molybdate, iron(II) oxalate dehydrate, iron(II) oxide, iron(II,III) oxide, iron(II) perchlorate hydrate, iron(II) phthalocyanine, iron(II) phthalocyanine bis(pyridine) complex, iron(II) sulfate heptahydrate, iron(II) sulfate hydrate, iron(II) sulfide, iron(II) tetrafluoroborate hexahydrate, iron(II) titanate, ammonium iron (II) sulfate hexahydrate, ammonium iron(II) sulfate, cyclopentadienyl iron(II) dicarbonyl dimer, ethylenediaminetetraacetic acid hydrate iron(III) sodium salt and ferric citrate.

Exemplary iron (III) compounds include iron(III) acetylacetonate, iron(III) bromide, iron(III) chloride, iron(III) chloride hexahydrate, iron(III) chloride solution, iron(III) chloride on silica gel, iron(III) citrate, tribasic monohydrate, iron(III) ferrocyanide, iron(III) fluoride, iron(III) fluoride trihydrate, iron(III) nitrate nonahydrate, iron(III) nitrate on silica gel, iron(III) oxalate hexahydrate, iron(III) oxide, iron (III) perchlorate hydrate, iron(III) phosphate, iron(III) phosphate dehydrate, iron(III) phosphate hydrate, iron(III) phosphate tetrahydrate, iron(III) phthalocyanine chloride, iron (III) phthalocyanine-4,4',4",4"-tetrasulfonic acid, compound with oxygen hydrate monosodium salt, iron(III) pyrophosphate, iron(III) sulfate hydrate, iron(III) p-toluenesulfonate hexahydrate, iron(III) tris(2,2,6,6-tetramethyl-3,5-heptanedionate) and ammonium iron(III) citrate.

Exemplary cobalt (II) compounds include cobalt(II) acetate, cobalt(II) acetate tetrahydrate, cobalt(II) acetylacetonate hydrate, cobalt(II) benzoylacetonate, cobalt(II) bromide, cobalt(II) bromide hydrate and cobalt(II) carbonate hydrate.

Exemplary cobalt (III) compounds include cobalt(III) acetylacetonate, cobalt(III) fluoride, cobalt(III) oxide, cobalt (III) sepulchrate trichloride, hexamine cobalt(III) chloride, bis(cyclopentadienyl)cobalt(III) hexafluorophosphate and bis(ethylcyclopentadienyl)cobalt(III) hexafluorophosphate.

Exemplary oxidants include peroxides, such as hydrogen peroxide and benzoyl peroxide, persulfates, such as ammonium persulfate, activated forms of oxygen, such as ozone, permanganates, such as potassium permanganate, perchlorates, such as sodium perchlorate, and hypochlorites, such as sodium hypochlorite (household bleach).

Generally, Fenton oxidation occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

In some cases, pH is maintained at or below about 5.5 during contact, such as between 1 and 5, between 2 and 5, between 2.5 and 5 or between about 3 and 5. The contact period may be, for example, between 2 and 12 hours, e.g., between 4 and 10 hours or between 5 and 8 hours. In some instances, the reaction conditions are controlled so that the temperature does not exceed 300° C., e.g., the temperature remains less than 250, 200, 150, 100 or even less than 50° C. In some cases, the temperature remains substantially ambient, e.g., at or about 20-25° C.

Figure 4:
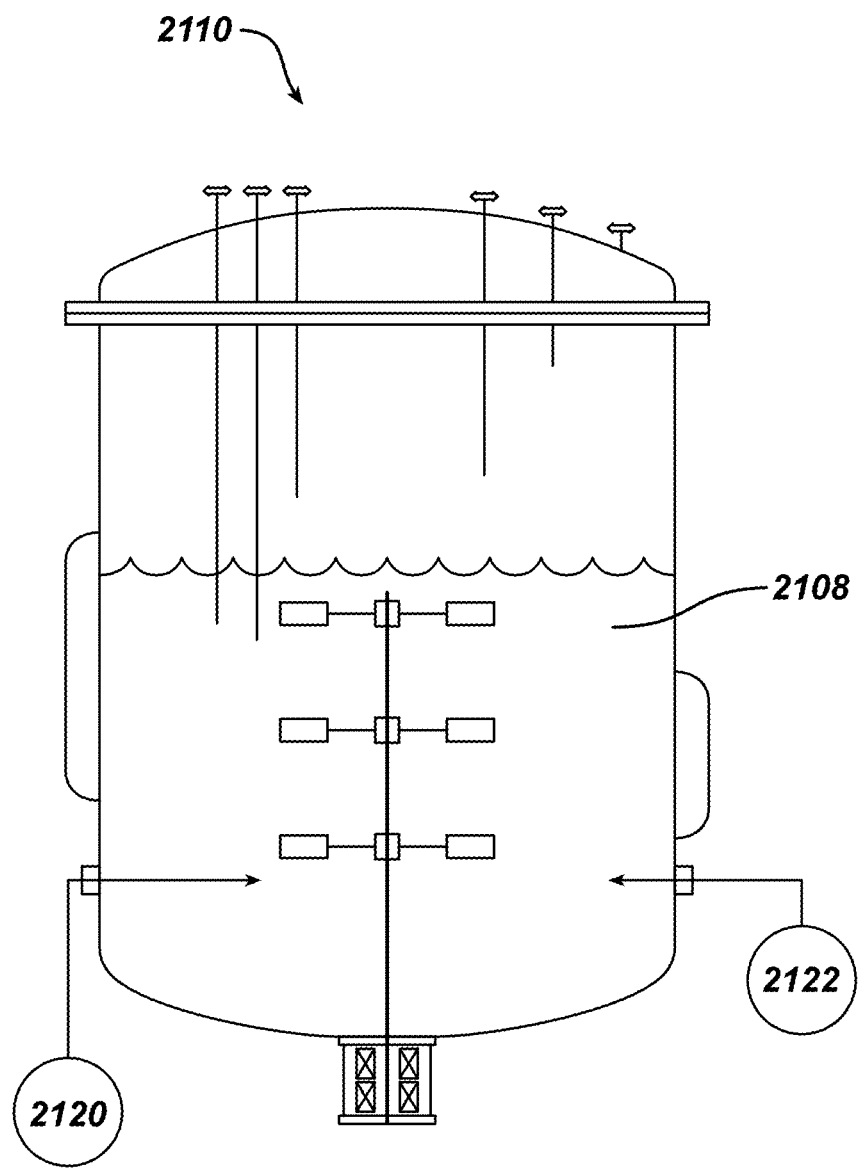
FIG. 4 is a schematic cross-sectional side view of a reactor.

Referring to FIG. 4, reactive mixtures 2108 within a vessel 2110 can be prepared using various approaches. For example, in instances in which the mixture includes one or more compounds and one or more oxidants, the first cellulosic or lignocellulosic material can be first dispersed in water or an aqueous medium, and then the one or more compounds can be added, followed by addition of the one or more oxidants. Alternatively, the one or more oxidants can added, followed by the one or more compounds, or the one or more oxidants and the one or more compounds can be concurrently added separately to the dispersion (e.g., each added independently through a separate addition device 2120, 2122 to the dispersion).

In some embodiments, a total maximum concentration of the elements in the one or more compounds measured in the dispersion is from about 10 μM to about 500 mM, e.g., between about 25 µM and about 250 mM or between about 100 µM and about 100 mM, and/or a total maximum concentration of the one or more oxidants is from about 100 µM to about 1 M, e.g., between about 250 µM and about 500 mM, or between about 500 µm and 250 mM. In some embodiments, the mole ratio of the elements in the one or more compounds to the one or more oxidants is from about 1:1000 to about 1:25, such as from about 1:500 to about 1:25 or from about 1:100 to about 1:25.

In some cases, the one or more oxidants are applied to the first cellulosic or lignocellulosic material and the one or more compounds as a gas, such as by generating ozone in-situ by irradiating the first cellulosic or lignocellulosic and the one or more compounds through air with a beam of particles, such as electrons or protons.

In other cases, the first cellulosic or lignocellulosic material is first dispersed in water or an aqueous medium that includes the one or more compounds dispersed and/or dissolved therein, and then water is removed after a soak time (e.g., loose and free water is removed by filtration), and then the one or more oxidants are applied to the combination as a gas, such as by generating ozone in-situ by irradiating the first cellulosic or lignocellulosic and the one or more compounds through air with a beam of particles, such as electrons (e.g., each being accelerated by a potential difference of between 3 MeV and 10 MeV).

Figure 5:
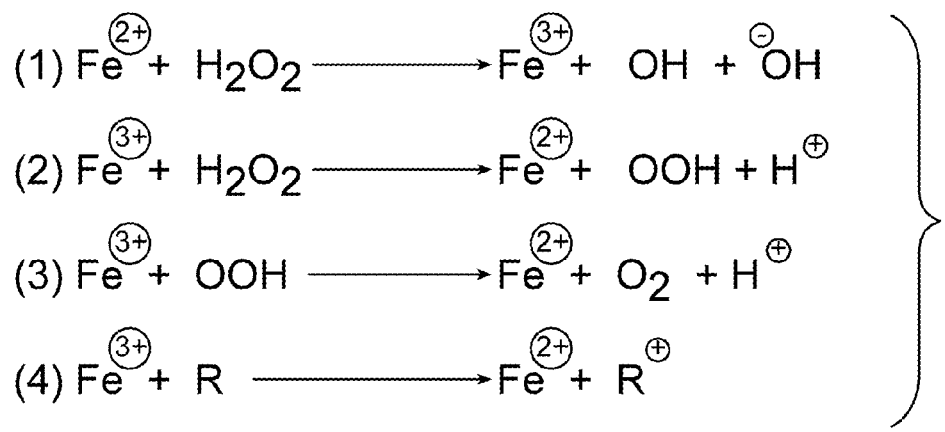
FIG. 5 shows a sequence of chemical reactions illustrating Fenton chemistry.

Referring now to FIG. 5, in some particular embodiments, an iron (II) compound is utilized for the Fenton-type chemistry, such as iron (II) sulfate, and hydrogen peroxide is utilized as the oxidant. FIG. 5 illustrates that in such a system, hydrogen peroxide oxidizes the iron (II) to generate iron (III), hydroxyl radicals and hydroxide ions (equation 1). The hydroxyl radicals can then react with the first cellulosic or lignocellulosic material, thereby oxidizing it to the second cellulosic or lignocellulosic material. The iron (III) thus produced can be reduced back to iron (II) by the action of hydrogen peroxide and hydroperoxyl radicals (equations 2 and 3). Equation 4 illustrates that it is also possible for an organic radical (R) to reduce iron (III) back to iron (II).

Figure 6:
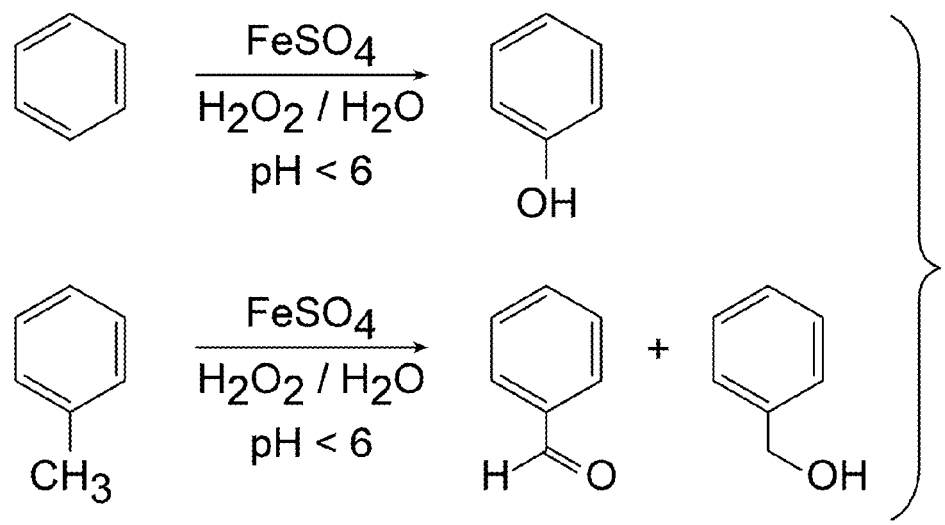
FIG. 6 shows a sequence of Fenton reactions illustrating conversion of benzene to phenol and toluene to benzaldehyde and benzyl alcohol.

FIG. 6 illustrates that iron (II) sulfate and hydrogen peroxide in aqueous solutions and at pH below about 6 can oxidize aromatic rings to give phenols, aldehydes and alcohols. When applied to cellulosic or lignocellulosic material, these Fenton-type reactions can help enhance the solubility of the lignocellulosic material by functionalization of the lignin and/or cellulose or hemicellulose, and by reduction in molecular weight of the lignocellulosic material. The net effect of the Fenton-type reactions on the lignocellulosic material can be a change in molecular structure and/or a reduction in its recalcitrance.

Figure 7:
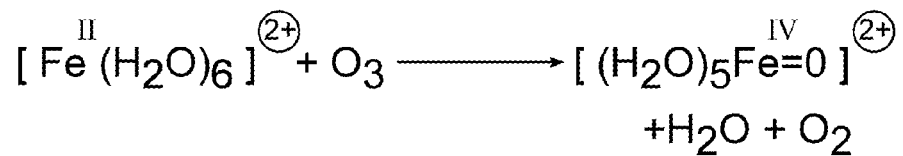
FIG. 7 shows a reaction scheme for the preparation of a reactive iron (IV) compound from an iron (II) compound.

FIG. 7 shows that hydrated iron (II) compounds, such as hydrated iron (II) sulfate, can react with ozone in aqueous solutions to generate extremely reactive hydrated iron (IV) compounds that can react with and oxidize cellulosic and lignocellulosic materials.

Figure 8:
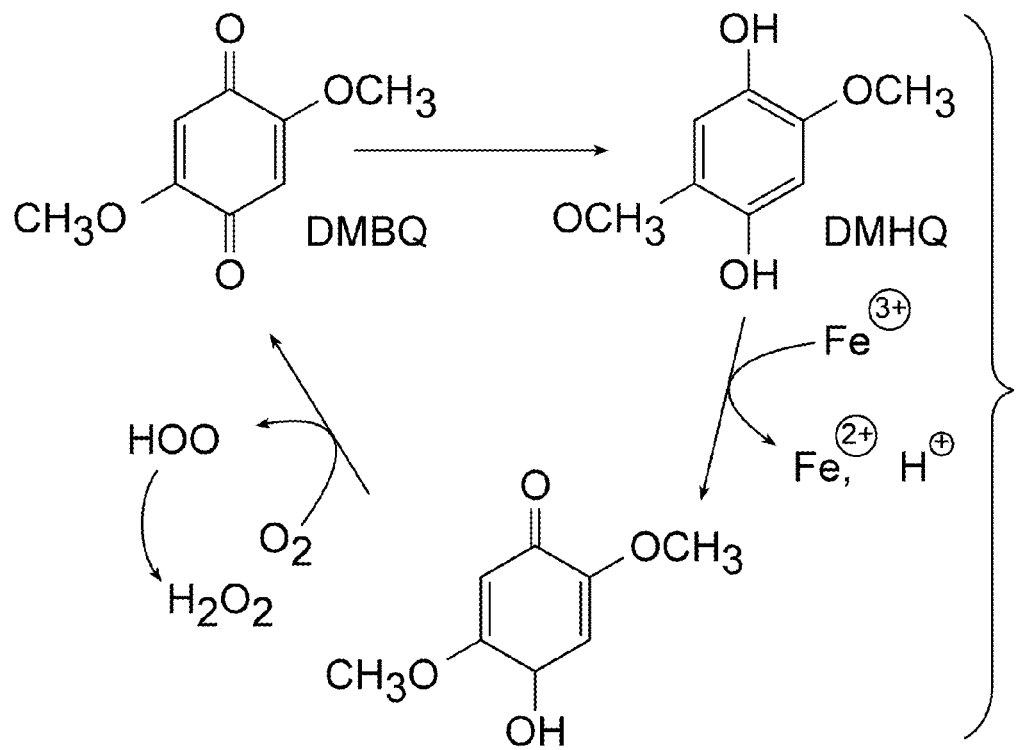
FIG. 8 shows a proposed pathway for reduction of Fe (III) and production of hydrogen peroxide in the presence of 2,5-dimethoxyhydroquinone.

In some desirable embodiments, the mixture further includes one or more hydroquinones, such as 2,5-dimethoxyhydroquinone (DMHQ) and/or one or more benzoquinones, such as 2,5-dimethoxy-1,4-benzoquinone (DMBQ), which can aid in electron transfer reactions. FIG. 8 illustrates how iron (III) can be reduced by DMHQ to give iron (II) and DMHQ semi-quinone radical. Addition of oxygen to the semi-quinone then gives alpha-hydroxyperoxyl radical that eliminates HOO. to give DMBQ. Finally, HOO. oxidizes iron (II) or dismutates to generate hydrogen peroxide.

In some desirable embodiments, the one or more oxidants are electrochemically or electromagnetically generated in-situ. For example, hydrogen peroxide and/or ozone can be electrochemically or electromagnetically produced within a contact or reaction vessel.

In some implementations, the Fenton reaction vessel may be portable, e.g., in the manner of the mobile processing equipment described in U.S. Provisional Patent Application Ser. No. 60/832,735, now Published International Application No. WO 2008/011598.

Radiation Treatment

Before, during or after the Fenton oxidation discussed above, one or more irradiation processing sequences can be used to pretreat the feedstock. Irradiation can reduce the molecular weight and/or crystallinity of feedstock. In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock. The doses applied depend on the desired effect and the particular feedstock. For example, high doses of radiation can break chemical bonds within feedstock components and low doses of radiation can increase chemical bonding (e.g., cross-linking) within feedstock components. In some instances when chain scission is desirable and/or polymer chain functionalization is desirable, particles heavier than electrons, such as protons, helium nuclei, argon ions, silicon ions, neon ions carbon ions, phosphorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized.

Doses

In some embodiments, the irradiating (with any radiation source or a combination of sources) is performed until the material receives a dose of at least 0.25 Mrad, e.g., at least 1.0 Mrad, 2.5 Mrad, 5.0 Mrad, 10.0 Mrad, 25 Mrad, 50 Mrad, or even at least 100 Mrad. In some embodiments, the irradiating is performed until the material receives a dose of between 1.0 Mrad and 6.0 Mrad, e.g., between 1.5 Mrad and 4.0 Mrad.

In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm.

In some embodiments, relatively low doses of radiation can crosslink, graft, or otherwise increase the molecular weight of a carbohydrate-containing material, such as a cellulosic or lignocellulosic material (e.g., cellulose). For example, a fibrous material that includes a first cellulosic and/or lignocellulosic material having a first molecular weight can be irradiated in such a manner as to provide a second cellulosic and/or lignocellulosic material having a second molecular weight higher than the first molecular weight. For example, if gamma radiation is utilized as the radiation source, a dose of from about 1 Mrad to about 10 Mrad, about 1 Mrad to about 75 Mrad, or about 1 Mrad to about 100 Mrad can be applied. In some implementations, from about 1.5 Mrad to about 7.5 Mrad or from about 2.0 Mrad to about 5.0 Mrad, can be applied.

Sonication, Pyrolysis, Oxidation, and Steam Explosion

One or more sonication, pyrolysis, oxidative processing, and/or steam explosion can be used to further pretreat the feedstock. Such processing can reduce the molecular weight and/or crystallinity of feedstock and biomass, e.g., one or more carbohydrate sources, such as cellulosic or lignocellulosic materials, or starchy materials. These processes are described in detail in U.S. Ser. No. 12/429,045.

In some embodiments, biomass can be processed by applying two or more of any of the processes described herein, such Fenton oxidation combined with any one, two or more of radiation, sonication, oxidation, pyrolysis, and steam explosion either with or without prior, intermediate, or subsequent physical feedstock preparation. The processes can be applied in any order or concurrently to the biomass. Multiple processes can in some cases provide materials that can be more readily utilized by a variety of microorganisms because of their lower molecular weight, lower crystallinity, and/or enhanced solubility. Multiple processes can provide synergies and can reduce overall energy input required in comparison to any single process.

Primary Processing

Primary processing of the pretreated feedstock may include bioprocesses such as saccharifying and/or fermenting the feedstock, e.g., by contacting the pretreated material with an enzyme and/or microorganism. Products produced by such contact can include any of those products described herein, such as food or fuel, e.g., ethanol, or any other products described in U.S. Provisional Application Ser. No. 61/139,453.

Fermentation

Generally, various microorganisms can produce a number of useful products, such as a fuel, by operating on, e.g., fermenting the pretreated biomass materials. For example, alcohols, organic acids, hydrocarbons, hydrogen, proteins or mixtures of any of these materials can be produced by fermentation or other bioprocesses.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

To aid in the breakdown of the materials that include the cellulose, one or more enzymes, e.g., a cellulolytic enzyme can be utilized. In some embodiments, the materials that include the cellulose are first treated with the enzyme, e.g., by combining the material and the enzyme in an aqueous solution. This material can then be combined with the microorganism. In other embodiments, the materials that include the cellulose, the one or more enzymes and the microorganism are combined concurrently, e.g., by combining in an aqueous solution.

The pretreated material can be treated with heat and/or a chemical (e.g., mineral acid, base or a strong oxidizer such as sodium hypochlorite) to further facilitate breakdown.

During fermentation, sugars released from cellulolytic hydrolysis or saccharification are fermented to, e.g., ethanol, by a fermenting microorganism such as yeast. Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Sacchromyces* spp. e.g., *Sacchromyces cerevisiae* (baker's yeast), *Saccharomyces distaticus, Saccharomyces uvarum*; the genus *Kluyveromyces*, e.g., species *Kluyveromyces marxianus, Kluyveromyces fragilis*; the genus *Candida*, e.g., *Candida pseudotropicalis*, and *Candida brassicae*, the genus *Clavispora*, e.g., species *Clavispora lusitaniae* and *Clavispora opuntiae* the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212).

Commercially available yeasts include, for example, Red Star®/Lesaffre Ethanol Red (available from Red Star/Lesaffre, USA) FALI® (available from Fleischmann's Yeast, a division of Burns Philip Food Inc., USA), SUPERSTART® (available from Alltech), GERT STRAND® (available from Gert Strand AB, Sweden) and FERMOL® (available from DSM Specialties).

Bacteria that can ferment biomass to ethanol and other products include, e.g., *Zymomonas mobilis* and *Clostridium thermocellum* (Philippidis, 1996, supra). Leschine et al. (*International Journal of Systematic and Evolutionary Microbiology* 2002, 52, 1155-1160) isolated an anaerobic, mesophilic, cellulolytic bacterium from forest soil, *Clostridium phytofermentans* sp. nov., which converts cellulose to ethanol.

Fermentation of biomass to ethanol and other products may be carried out using certain types of thermophilic or genetically engineered microorganisms, such *Thermoanaerobacter* species, including *T. mathranii*, and yeast species such as *Pichia* species. An example of a strain of *T. mathranii* is A3M4 described in Sonne-Hansen et al. (*Applied Microbiology and Biotechnology* 1993, 38, 537-541) or Ahring et al. (*Arch. Microbiol.* 1997, 168, 114-119).

Yeast and *Zymomonas* bacteria can be used for fermentation or conversion. The optimum pH for yeast is from about pH 4 to 5, while the optimum pH for *Zymomonas* is from about pH 5 to 6. Typical fermentation times are about 24 to 96 hours with temperatures in the range of 26° C. to 40° C., however thermophilic microorganisms prefer higher temperatures.

Enzymes and biomass-destroying organisms that break down biomass, such as the cellulose and/or the lignin portions of the biomass, to lower molecular weight of the carbohydrate-containing materials contain or make various cellulolytic enzymes (cellulases), ligninases or various small molecule biomass-destroying metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (β-glucosidases). A cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose.

A cellulase is capable of degrading biomass and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Anaerobic cellulolytic bacteria have also been isolated from soil, e.g., a novel cellulolytic species of *Clostiridium, Clostridium phytofermentans* sp. nov. (see Leschine et. al, *International Journal of Systematic and Evolutionary Microbiology* (2002), 52, 1155-1160).

Cellulolytic enzymes using recombinant technology can also be used (see, e.g., WO 2007/071818 and WO 2006/110891).

The cellulolytic enzymes used can be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi, Academic Press*, CA 1991). Suitable media are available from commercial suppliers or may be prepared according to published compositions (e.g., in catalogues of the American Type Culture Collection). Temperature ranges and other conditions suitable for growth and cellulase production are known in the art (see, e.g., Bailey, J. E., and Ollis, D. F., *Biochemical Engineering Fundamentals*, McGraw-Hill Book Company, NY, 1986).

Treatment of cellulose with cellulase is usually carried out at temperatures between 30° C. and 65° C. Cellulases are active over a range of pH of about 3 to 7. A saccharification step may last up to 120 hours. The cellulase enzyme dosage achieves a sufficiently high level of cellulose conversion. For example, an appropriate cellulase dosage is typically between 5.0 and 50 Filter Paper Units (FPU or IU) per gram of cellulose. The FPU is a standard measurement and is defined and measured according to Ghose (1987, Pure and Appl. Chem. 59:257-268).

Mobile fermentors can be utilized, as described in U.S. Provisional Patent Application Ser. No. 60/832,735, now Published International Application No. WO 2008/011598.

Products/Co-Products

Using such primary processes and/or post-processing, the treated biomass can be converted to one or more products, for example alcohols, e.g., methanol, ethanol, propanol, isopropanol, butanol, e.g., n-, sec- or t-butanol, ethylene glycol, propylene glycol, 1,4-butane diol, glycerin or mixtures of these alcohols; organic acids, such as formic acid, acetic acid, propionic acid, butyric acid, valeric acid, caproic, palmitic acid, stearic acid, oxalic acid, malonic acid, succinic acid, glutaric acid, oleic acid, linoleic acid, glycolic acid, lactic acid, γ-hydroxybutyric acid or mixtures of these acids; food products; animal feed; pharmaceuticals; or nutriceuticals. Co-products that may be produced include lignin residue.

EXAMPLES

The following Examples are intended to illustrate, and do not limit the teachings of this disclosure.

Example 1

Preparation of Fibrous Material from Polycoated Paper

A 1500 pound skid of virgin, half-gallon juice cartons made of un-printed polycoated white Kraft board having a bulk density of 20 lb/ft$^3$ was obtained from International Paper. Each carton was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch).

Figure 9:
FIG. 9 is a scanning electron micrograph of a fibrous material produced from polycoated paper at 25× magnification. The fibrous material was produced on a rotary knife cutter utilizing a screen with 1/8 inch openings.

The confetti-like material was fed to a Munson rotary knife cutter, Model SC30. Model SC30 is equipped with four rotary blades, four fixed blades, and a discharge screen having ⅛ inch openings. The gap between the rotary and fixed blades was set to approximately 0.020 inch. The rotary knife cutter sheared the confetti-like pieces across the knife-edges, tearing the pieces apart and releasing a fibrous material at a rate of about one pound per hour. The fibrous material had a BET surface area of 0.9748 m$^2$/g+/−0.0167 m$^2$/g, a porosity of 89.0437 percent and a bulk density (@0.53 psia) of 0.1260 g/mL. An average length of the fibers was 1.141 mm and an average width of the fibers was 0.027 mm, giving an average L/D of 42:1. A scanning electron micrograph of the fibrous material is shown in FIG. 9 at 25× magnification.

Example 2

Preparation of Fibrous Material from Bleached Kraft Board

Figure 10:
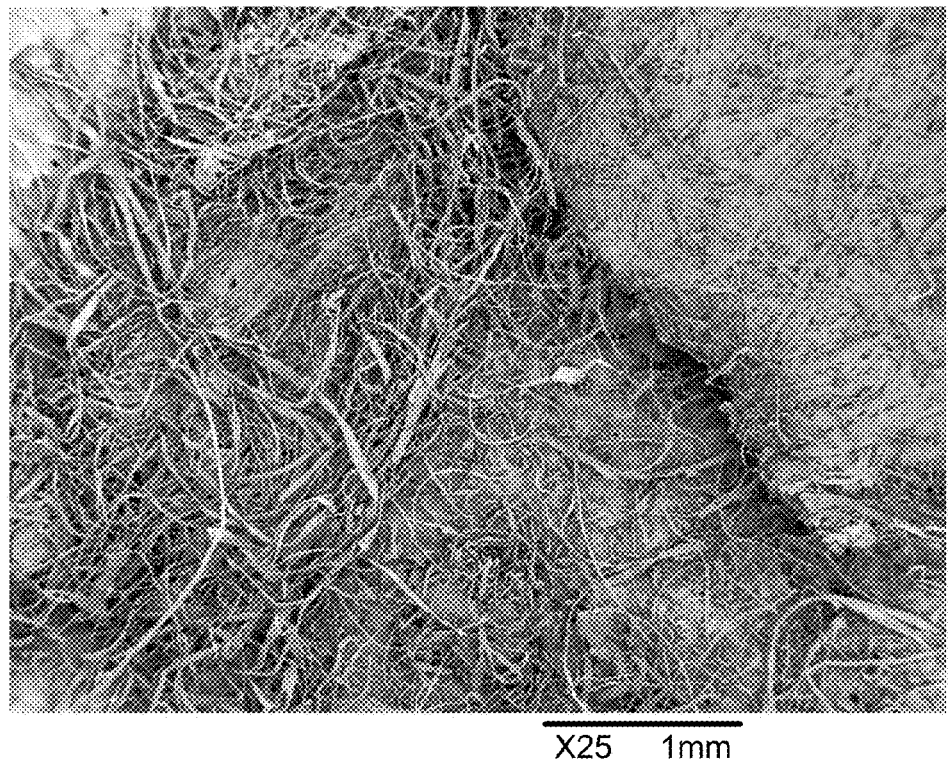
FIG. 10 is a scanning electron micrograph of a fibrous material produced from bleached Kraft board paper at 25× magnification. The fibrous material was produced on a rotary knife cutter utilizing a screen with 1/8 inch openings.

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch). The confetti-like material was fed to a Munson rotary knife cutter, Model SC30. The discharge screen had ⅛ inch openings. The gap between the rotary and fixed blades was set to approximately 0.020 inch. The rotary knife cutter sheared the confetti-like pieces, releasing a fibrous material at a rate of about one pound per hour. The fibrous material had a BET surface area of 1.1316 m²/g+/−0.0103 m²/g, a porosity of 88.3285 percent and a bulk density (@0.53 psia) of 0.1497 g/mL. An average length of the fibers was 1.063 mm and an average width of the fibers was 0.0245 mm, giving an average L/D of 43:1. A scanning electron micrographs of the fibrous material is shown in FIG. 10 at 25× magnification.

Example 3

Preparation of Twice Sheared Fibrous Material from Bleached Kraft Board

Figure 11:
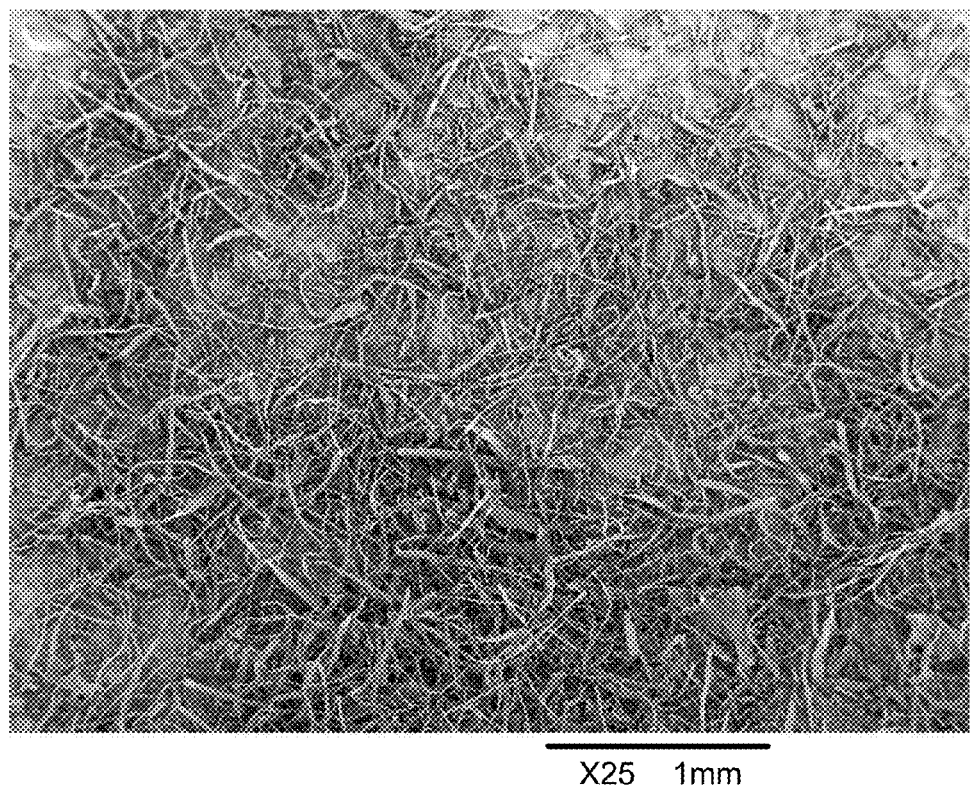
FIG. 11 is a scanning electron micrograph of a fibrous material produced from bleached Kraft board paper at 25× magnification. The fibrous material was twice sheared on a rotary knife cutter utilizing a screen with 1/16 inch openings during each shearing.

A 1500 pound skid of virgin bleached white Kraft board having a bulk density of 30 lb/ft³ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had 1/16 inch openings. The gap between the rotary and fixed blades was set to approximately 0.020 inch. The rotary knife cutter the confetti-like pieces, releasing a fibrous material at a rate of about one pound per hour. The material resulting from the first shearing was fed back into the same setup described above and sheared again. The resulting fibrous material had a BET surface area of 1.4408 m²/g+/− 0.0156 m²/g, a porosity of 90.8998 percent and a bulk density (@0.53 psia) of 0.1298 g/mL. An average length of the fibers was 0.891 mm and an average width of the fibers was 0.026 mm, giving an average L/D of 34:1. A scanning electron micrograph of the fibrous material is shown in FIG. 11 at 25× magnification.

Example 4

Preparation of Thrice Sheared Fibrous Material from Bleached Kraft Board

Figure 12:
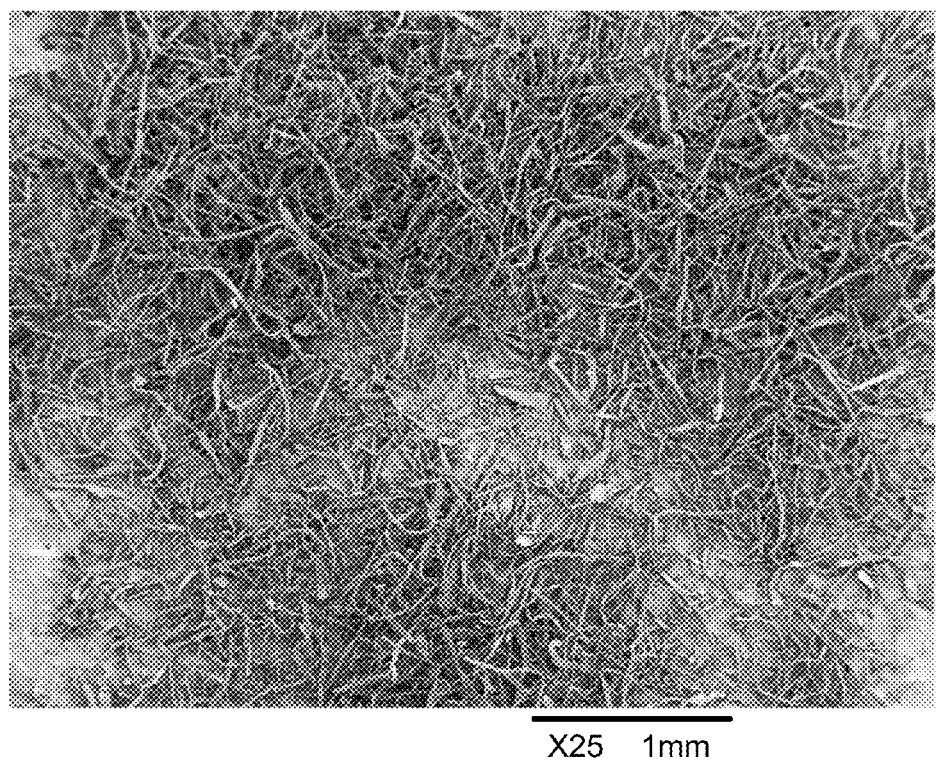
FIG. 12 is a scanning electron micrograph of a fibrous material produced from bleached Kraft board paper at 25× magnification. The fibrous material was thrice sheared on a rotary knife cutter. During the first shearing, a 1/8 inch screen was used; during the second shearing, a 1/16 inch screen was used, and during the third shearing a 1/32 inch screen was used.

A 1500 pound skid of virgin bleached white Kraft board having a bulk density of 30 lb/ft³ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had 1/8 inch openings. The gap between the rotary and fixed blades was set to approximately 0.020 inch. The rotary knife cutter sheared the confetti-like pieces across the knife-edges. The material resulting from the first shearing was fed back into the same setup and the screen was replaced with a 1/16 inch screen. This material was sheared. The material resulting from the second shearing was fed back into the same setup and the screen was replaced with a 1/32 inch screen. This material was sheared. The resulting fibrous material had a BET surface area of 1.6897 m²/g+/−0.0155 m²/g, a porosity of 87.7163 percent and a bulk density (@0.53 psia) of 0.1448 g/mL. An average length of the fibers was 0.824 mm and an average width of the fibers was 0.0262 mm, giving an average L/D of 32:1. A scanning electron micrograph of the fibrous material is shown in FIG. 12 at 25× magnification.

Example 5

Methods of Determining Molecular Weight of Cellulosic and Lignocellulosic Materials by Gel Permeation Chromatography Cellulosic and lignocellulosic materials for analysis were treated according to Example 4. Sample materials presented in the following tables include Kraft paper (P), wheat straw (WS), alfalfa (A), and switchgrass (SG). The number "132" of the Sample ID refers to the particle size of the material after shearing through a 1/32 inch screen. The number after the dash refers to the dosage of radiation (MRad) and "US" refers to ultrasonic treatment. For example, a sample ID "P132-10" refers to Kraft paper that has been sheared to a particle size of 132 mesh and has been irradiated with 10 MRad.

TABLE 1

Peak Average Molecular Weight of Irradiated Kraft Paper

| Sample Source | Sample ID | Dosage[1] (MRad) | Ultrasound[2] | Average MW ± Std. Dev. |
|---|---|---|---|---|
| Kraft Paper | P132 | 0 | No | 32853 ± 10006 |
| | P132-10 | 10 | " | 61398 ± 2468** |
| | P132-100 | 100 | " | 8444 ± 580 |
| | P132-181 | 181 | " | 6668 ± 77 |
| | P132-US | 0 | Yes | 3095 ± 1013 |

**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

TABLE 2

Peak Average Molecular Weight of Irradiated Materials

| Sample ID | Peak # | Dosage[1] (MRad) | Ultrasound[2] | Average MW ± Std. Dev. |
|---|---|---|---|---|
| WS132 | 1 | 0 | No | 1407411 ± 175191 |
| | 2 | " | " | 39145 ± 3425 |
| | 3 | " | " | 2886 ± 177 |
| WS132-10* | 1 | 10 | " | 26040 ± 3240 |
| WS132-100* | 1 | 100 | " | 23620 ± 453 |
| A132 | 1 | 0 | " | 1604886 ± 151701 |
| | 2 | " | " | 37525 ± 3751 |
| | 3 | " | " | 2853 ± 490 |
| A132-10* | 1 | 10 | " | 50853 ± 1665 |
| | 2 | " | " | 2461 ± 17 |
| A132-100* | 1 | 100 | " | 38291 ± 2235 |
| | 2 | " | " | 2487 ± 15 |
| SG132 | 1 | 0 | " | 1557360 ± 83693 |
| | 2 | " | " | 42594 ± 4414 |
| | 3 | " | " | 3268 ± 249 |
| SG132-10* | 1 | 10 | " | 60888 ± 9131 |
| SG132-100* | 1 | 100 | " | 22345 ± 3797 |
| SG132-10-US | 1 | 10 | Yes | 86086 ± 43518 |
| | 2 | " | " | 2247 ± 468 |
| SG132-100-US | 1 | 100 | " | 4696 ± 1465 |

*Peaks coalesce after treatment
**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

Gel Permeation Chromatography (GPC) is used to determine the molecular weight distribution of polymers. During GPC analysis, a solution of the polymer sample is passed through a column packed with a porous gel trapping small molecules. The sample is separated based on molecular size with larger molecules eluting sooner than smaller molecules. The retention time of each component is most often detected by refractive index (RI), evaporative light scattering (ELS), or ultraviolet (UV) and compared to a calibration curve. The resulting data is then used to calculate the molecular weight distribution for the sample.

A distribution of molecular weights rather than a unique molecular weight is used to characterize synthetic polymers. To characterize this distribution, statistical averages are utilized. The most common of these averages are the "number average molecular weight" ($M_n$) and the "weight average molecular weight" ($M_w$).

$M_n$ is similar to the standard arithmetic mean associated with a group of numbers. When applied to polymers, $M_n$ refers to the average molecular weight of the molecules in the polymer. $M_n$ is calculated affording the same amount of significance to each molecule regardless of its individual molecular weight. The average $M_n$ is calculated by the following formula where $N_i$ is the number of molecules with a molar mass equal to $M_i$.

$$\overline{M}_n = \frac{\sum_i N_i M_i}{\sum_i N_i}$$

$M_w$ is another statistical descriptor of the molecular weight distribution that places a greater emphasis on larger molecules than smaller molecules in the distribution. The formula below shows the statistical calculation of the weight average molecular weight.

$$\overline{M}_w = \frac{\sum_i N_i M_i^2}{\sum_i N_i M_i}$$

The polydispersity index or PI is defined as the ratio of $M_w/M_n$. The larger the PI, the broader or more disperse the distribution. The lowest value that a PI can be is 1. This represents a monodisperse sample; that is, a polymer with all of the molecules in the distribution being the same molecular weight.

The peak molecular weight value ($M_P$) is another descriptor defined as the mode of the molecular weight distribution. It signifies the molecular weight that is most abundant in the distribution. This value also gives insight to the molecular weight distribution.

Most GPC measurements are made relative to a different polymer standard. The accuracy of the results depends on how closely the characteristics of the polymer being analyzed matches those of the standard used. The expected error in reproducibility between different series of determinations, calibrated separately, is ca. 5-10% and is characteristic to the limited precision of GPC determinations. Therefore, GPC results are most useful when a comparison between the molecular weight distribution of different samples is made during the same series of determinations.

The lignocellulosic samples required sample preparation prior to GPC analysis. First, a saturated solution (8.4% by weight) of lithium chloride (LiCl) was prepared in dimethyl acetamide (DMAc). Approximately 100 mg of the sample was added to approximately 10 g of a freshly prepared saturated LiCl/DMAc solution, and the mixture was heated to approximately 150° C.-170° C. with stirring for 1 hour. The resulting solutions were generally light- to dark-yellow in color. The temperature of the solutions were decreased to approximately 100° C. and heated for an additional 2 hours. The temperature of the solutions were then decreased to approximately 50° C. and the sample solution was heated for approximately 48 to 60 hours. Of note, samples irradiated at 100 MRad were more easily solubilized as compared to their untreated counterpart. Additionally, the sheared samples (denoted by the number 132) had slightly lower average molecular weights as compared with uncut samples.

The resulting sample solutions were diluted 1:1 using DMAc as solvent and were filtered through a 0.45 μm PTFE filter. The filtered sample solutions were then analyzed by GPC. The peak average molecular weight (Mp) of the samples, as determined by Gel Permeation Chromatography (GPC), are summarized in Tables 1 and 2. Each sample was prepared in duplicate and each preparation of the sample was analyzed in duplicate (two injections) for a total of four injections per sample. The EASICAL® polystyrene standards PS1A and PS1B were used to generate a calibration curve for the molecular weight scale from about 580 to 7,500,000 Daltons. Table 3 recites the GPC analysis conditions.

TABLE 3

| GPC Analysis Conditions | |
|---|---|
| Instrument: | Waters Alliance GPC 2000 Plgel 10μ Mixed-B |
| Columns (3): | S/N's: 10M-MB-148-83; 10M-MB-148-84; 10M-MB-174-129 |
| Mobile Phase (solvent): | 0.5% LiCl in DMAc (1.0 mL/min) |
| Column/Detector Temperature: | 70° C. |
| Injector Temperature: | 70° C. |
| Sample Loop Size: | 323.5 μL |

Example 6

Porosimetry Analysis of Irradiated Materials

Mercury pore size and pore volume analysis (Table 4) is based on forcing mercury (a non-wetting liquid) into a porous structure under tightly controlled pressures. Since mercury does not wet most substances and will not spontaneously penetrate pores by capillary action, it must be forced into the voids of the sample by applying external pressure. The pressure required to fill the voids is inversely proportional to the size of the pores. Only a small amount of force or pressure is required to fill large voids, whereas much greater pressure is required to fill voids of very small pores.

TABLE 4

| Pore Size and Volume Distribution by Mercury Porosimetry | | | | | | | | |
|---|---|---|---|---|---|---|---|---|
| Sample ID | Total Intrusion Volume (mL/g) | Total Pore Area (m²/g) | Median Pore Diameter (Volume) (μm) | Median Pore Diameter (Area) (μm) | Average Pore Diameter (4 V/A) (μm) | Bulk Density @ 0.50 psia (g/mL) | Apparent (skeletal) Density (g/mL) | Porosity (%) |
| P132 | 6.0594 | 1.228 | 36.2250 | 13.7278 | 19.7415 | 0.1448 | 1.1785 | 87.7163 |
| P132-10 | 5.5436 | 1.211 | 46.3463 | 4.5646 | 18.3106 | 0.1614 | 1.5355 | 89.4875 |

TABLE 4-continued

Pore Size and Volume Distribution by Mercury Porosimetry

| Sample ID | Total Intrusion Volume (mL/g) | Total Pore Area (m²/g) | Median Pore Diameter (Volume) (μm) | Median Pore Diameter (Area) (μm) | Average Pore Diameter (4 V/A) (μm) | Bulk Density @ 0.50 psia (g/mL) | Apparent (skeletal) Density (g/mL) | Porosity (%) |
|---|---|---|---|---|---|---|---|---|
| P132-100 | 5.3985 | 0.998 | 34.5235 | 18.2005 | 21.6422 | 0.1612 | 1.2413 | 87.0151 |
| P132-181 | 3.2866 | 0.868 | 25.3448 | 12.2410 | 15.1509 | 0.2497 | 1.3916 | 82.0577 |
| P132-US | 6.0005 | 14.787 | 98.3459 | 0.0055 | 1.6231 | 0.1404 | 0.8894 | 84.2199 |
| A132 | 2.0037 | 11.759 | 64.6308 | 0.0113 | 0.6816 | 0.3683 | 1.4058 | 73.7990 |
| A132-10 | 1.9514 | 10.326 | 53.2706 | 0.0105 | 0.7560 | 0.3768 | 1.4231 | 73.5241 |
| A132-100 | 1.9394 | 10.205 | 43.8966 | 0.0118 | 0.7602 | 0.3760 | 1.3889 | 72.9264 |
| SG132 | 2.5267 | 8.265 | 57.6958 | 0.0141 | 1.2229 | 0.3119 | 1.4708 | 78.7961 |
| SG132-10 | 2.1414 | 8.643 | 26.4666 | 0.0103 | 0.9910 | 0.3457 | 1.3315 | 74.0340 |
| SG132-100 | 2.5142 | 10.766 | 32.7118 | 0.0098 | 0.9342 | 0.3077 | 1.3590 | 77.3593 |
| SG132-10-US | 4.4043 | 1.722 | 71.5734 | 1.1016 | 10.2319 | 0.1930 | 1.2883 | 85.0169 |
| SG132-100-US | 4.9665 | 7.358 | 24.8462 | 0.0089 | 2.6998 | 0.1695 | 1.0731 | 84.2010 |
| WS132 | 2.9920 | 5.447 | 76.3675 | 0.0516 | 2.1971 | 0.2773 | 1.6279 | 82.9664 |
| WS132-10 | 3.1138 | 2.901 | 57.4727 | 0.3630 | 4.2940 | 0.2763 | 1.9808 | 86.0484 |
| WS132-100 | 3.2077 | 3.114 | 52.3284 | 0.2876 | 4.1199 | 0.2599 | 1.5611 | 83.3538 |

The AUTOPORE® 9520 can attain a maximum pressure of 414 MPa or 60,000 psia. There are four low pressure stations for sample preparation and collection of macropore data from 0.2 psia to 50 psia. There are two high pressure chambers which collects data from 25 psia to 60,000 psia. The sample is placed in a bowl-like apparatus called a penetrometer, which is bonded to a glass capillary stem with a metal coating. As mercury invades the voids in and around the sample, it moves down the capillary stem. The loss of mercury from the capillary stem results in a change in the electrical capacitance. The change in capacitance during the experiment is converted to volume of mercury by knowing the stem volume of the penetrometer in use. A variety of penetrometers with different bowl (sample) sizes and capillaries are available to accommodate most sample sizes and configurations. Table 5 below defines some of the key parameters calculated for each sample.

TABLE 5

Definition of Parameters

| Parameter | Description |
|---|---|
| Total Intrusion Volume: | The total volume of mercury intruded during an experiment. This can include interstitial filling between small particles, porosity of sample, and compression volume of sample. |
| Total Pore Area | The total intrusion volume converted to an area assuming cylindrical shaped pores. |
| Median Pore Diameter (volume): | The size at the 50$^{th}$ percentile on the cumulative volume graph. |
| Median Pore Diameter (area): | The size at the 50$^{th}$ percentile on the cumulative area graph. |
| Average Pore Diameter: | The total pore volume divided by the total pore area (4 V/A). |
| Bulk Density: | The mass of the sample divided by the bulk volume. Bulk volume is determined at the filling pressure, typically 0.5 psia. |
| Apparent Density: | The mass of sample divided by the volume of sample measured at highest pressure, typically 60,000 psia. |
| Porosity: | (Bulk Density/Apparent Density) × 100% |

Example 7

Particle Size Analysis of Irradiated Materials

The technique of particle sizing by static light scattering is based on Mie theory (which also encompasses Fraunhofer theory). Mie theory predicts the intensity vs. angle relationship as a function of the size for spherical scattering particles provided that other system variables are known and held constant. These variables are the wavelength of incident light and the relative refractive index of the sample material. Application of Mie theory provides the detailed particle size information. Table 6 summarizes particle size using median diameter, mean diameter, and modal diameter as parameters.

TABLE 6

Particle Size by Laser Light Scattering (Dry Sample Dispersion)

| Sample ID | Median Diameter (μm) | Mean Diameter (μm) | Modal Diameter (μm) |
|---|---|---|---|
| A132 | 380.695 | 418.778 | 442.258 |
| A132-10 | 321.742 | 366.231 | 410.156 |
| A132-100 | 301.786 | 348.633 | 444.169 |
| SG132 | 369.400 | 411.790 | 455.508 |
| SG132-10 | 278.793 | 325.497 | 426.717 |
| SG132-100 | 242.757 | 298.686 | 390.097 |
| WS132 | 407.335 | 445.618 | 467.978 |

TABLE 6-continued

Particle Size by Laser Light Scattering (Dry Sample Dispersion)

| Sample ID | Median Diameter (μm) | Mean Diameter (μm) | Modal Diameter (μm) |
|---|---|---|---|
| WS132-10 | 194.237 | 226.604 | 297.941 |
| WS132-100 | 201.975 | 236.037 | 307.304 |

Particle size was determined by Laser Light Scattering (Dry Sample Dispersion) using a Malvern Mastersizer 2000 using the following conditions:

| Feed Rate: | 35% |
|---|---|
| Disperser Pressure: | 4 Bar |
| Optical Model: | (2.610, 1.000i), 1.000 |

An appropriate amount of sample was introduced onto a vibratory tray. The feed rate and air pressure were adjusted to ensure that the particles were properly dispersed. The key component is selecting an air pressure that will break up agglomerations, but does not compromise the sample integrity. The amount of sample needed varies depending on the size of the particles. In general, samples with fine particles require less material than samples with coarse particles.

Example 8

Surface Area Analysis of Irradiated Materials

Surface area of each sample was analyzed using a MICROMERITICS® ASAP 2420 Accelerated Surface Area and Porosimetry System. The samples were prepared by first degassing for 16 hours at 40° C. Next, free space (both warm and cold) with helium is calculated and then the sample tube is evacuated again to remove the helium. Data collection begins after this second evacuation and consists of defining target pressures which controls how much gas is dosed onto the sample. At each target pressure, the quantity of gas adsorbed and the actual pressure are determined and recorded. The pressure inside the sample tube is measured with a pressure transducer. Additional doses of gas will continue until the target pressure is achieved and allowed to equilibrate. The quantity of gas adsorbed is determined by summing multiple doses onto the sample. The pressure and quantity define a gas adsorption isotherm and are used to calculate a number of parameters, including BET surface area (Table 7).

TABLE 7

Summary of Surface Area by Gas Adsorption

| Sample ID | Single point surface area (m²/g) | | BET Surface Area (m²/g) |
|---|---|---|---|
| P132 | @ P/Po = 0.250387771 | 1.5253 | 1.6897 |
| P132-10 | @ P/Po = 0.239496722 | 1.0212 | 1.2782 |
| P132-100 | @ P/Po = 0.240538100 | 1.0338 | 1.2622 |
| P132-181 | @ P/Po = 0.239166091 | 0.5102 | 0.6448 |
| P132-US | @ P/Po = 0.217359072 | 1.0983 | 1.6793 |
| A132 | @ P/Po = 0.240040610 | 0.5400 | 0.7614 |
| A132-10 | @ P/Po = 0.211218936 | 0.5383 | 0.7212 |
| A132-100 | @ P/Po = 0.238791097 | 0.4258 | 0.5538 |
| SG132 | @ P/Po = 0.237989353 | 0.6359 | 0.8350 |
| SG132-10 | @ P/Po = 0.238576905 | 0.6794 | 0.8689 |
| SG132-100 | @ P/Po = 0.241960361 | 0.5518 | 0.7034 |
| SG132-10-US | @ P/Po = 0.225692889 | 0.5693 | 0.7510 |
| SG132-100-US | @ P/Po = 0.225935246 | 1.0983 | 1.4963 |

TABLE 7-continued

Summary of Surface Area by Gas Adsorption

| Sample ID | Single point surface area (m²/g) | | BET Surface Area (m²/g) |
|---|---|---|---|
| WS132 | @ P/Po = 0.237823664 | 0.6582 | 0.8663 |
| WS132-10 | @ P/Po = 0.238612476 | 0.6191 | 0.7912 |
| WS132-100 | @ P/Po = 0.238398832 | 0.6255 | 0.8143 |

The BET model for isotherms is a widely used theory for calculating the specific surface area. The analysis involves determining the monolayer capacity of the sample surface by calculating the amount required to cover the entire surface with a single densely packed layer of krypton. The monolayer capacity is multiplied by the cross sectional area of a molecule of probe gas to determine the total surface area. Specific surface area is the surface area of the sample aliquot divided by the mass of the sample.

Example 9

Fiber Length Determination of Irradiated Materials

Fiber length distribution testing was performed in triplicate on the samples submitted using the Techpap MorFi LB01 system. The average length and width are reported in Table 8.

TABLE 8

Summary of Lignocellulosic Fiber Length and Width Data

| Sample ID | Arithmetic Average (mm) | Average Length Weighted in Length (mm) | Statistically Corrected Average Length Weighted in Length (mm) | Width (micrometers) (μm) |
|---|---|---|---|---|
| P132-10 | 0.484 | 0.615 | 0.773 | 24.7 |
| P132-100 | 0.369 | 0.423 | 0.496 | 23.8 |
| P132-181 | 0.312 | 0.342 | 0.392 | 24.4 |
| A132-10 | 0.382 | 0.423 | 0.650 | 43.2 |
| A132-100 | 0.362 | 0.435 | 0.592 | 29.9 |
| SG132-10 | 0.328 | 0.363 | 0.521 | 44.0 |
| SG132-100 | 0.325 | 0.351 | 0.466 | 43.8 |
| WS132-10 | 0.353 | 0.381 | 0.565 | 44.7 |
| WS132-100 | 0.354 | 0.371 | 0.536 | 45.4 |

Other Embodiments

A number of embodiments of the invention have been described. Nevertheless, it will be understood that various modifications may be made without departing from the spirit and scope of the invention.

Lignases and Biomass Destroying Enzymes

For example, some methods utilize one or more ligninases and/or biomass-destroying enzymes, instead of or in addition to Fenton chemistry, to reduce recalcitrance in cellulosic or lignocellulosic materials. In such methods, a first cellulosic or lignocellulosic material having a first level of recalcitrance is provided and combined with one or more ligninases and/or one or more biomass-destroying, e.g., lignin-destroying organisms, so as to contact the first cellulosic or lignocellulosic material. The contact is maintained for a period of time, such as between 2 and 24 hours, e.g., between 6 and 12 hours, and under conditions sufficient, e.g., below a pH of about 6, such as between pH 3 and 5.5, to produce a second lignocellulosic material having a second level of recalcitrance lower than the first level of recalcitrance. After reduction of the recalcitrance, the second cellulosic or lignocellulosic material can be contacted with one or more enzymes and/or microorganisms, e.g., to make any product described herein, e.g., food or fuel, e.g., ethanol or butanol (e.g., n-butanol) or any product described in any application incorporated by reference herein.

The ligninase can be, e.g., one or more of manganese peroxidase, lignin peroxidase or laccases.

In particular implementations, the biomass-destroying organism can be, e.g., one or more of white rot, brown rot or soft rot. For example, the biomass-destroying organism can be a Basidiomycetes fungus. In particular embodiments, the biomass-destroying organism *Phanerochaete chrysoporium* or *Gleophyllum trabeum*.

Ligninases, biomass-destroying organisms and small molecule metabolites are described in Kirk et al., Enzyme Microb. Technol. 1986, vol. 8, 27-32, Kirk et al., Enzymes for Pulp and Paper Processing, Chapter 1 (Roles for Microbial Enzymes in Pulp and Paper Processing and Kirk et al., The Chemistry of Solid Wood, Chapter 12 (Biological Decomposition of Solid Wood (pp. 455-487).

Hydrocarbon-Containing Materials

In some embodiments, the methods and systems disclosed herein can be used to process hydrocarbon-containing materials such as tar or oil sands, oil shale, crude oil (e.g., heavy crude oil and/or light crude oil), bitumen, coal, petroleum gases (e.g., methane, ethane, propane, butane, isobutane), liquefied natural and/or synthetic gas, asphalt, and other natural materials that include various types of hydrocarbons. For example, a processing facility for hydrocarbon-containing materials receives a supply of raw material. The raw material can be delivered directly from a mine, e.g., by conveyor belt and/or rail car system, and in certain embodiments, the processing facility can be constructed in relatively close proximity to, or even atop, the mine. In some embodiments, the raw material can be transported to the processing facility via railway freight car or another motorized transport system, and/or pumped to the processing facility via pipeline.

When the raw material enters the processing facility, the raw material can be broken down mechanically and/or chemically to yield starting material. As an example, the raw material can include material derived from oil sands and containing crude bitumen. Bitumen can then be processed into one or more hydrocarbon products using the methods disclosed herein. In some embodiments, the oil sands material can be extracted from surface mines such as open pit mines. In certain embodiments, sub-surface oil sands material can be extracted using a hot water flotation process that removes oil from sand particles, and then adding naphtha to allow pumping of the oil to the processing facility.

Bitumen processing generally includes two stages. In a first stage, relatively large bitumen hydrocarbons are cracked into smaller molecules using coking, hydrocracking, or a combination of the two techniques. In the coking process, carbon is removed from bitumen hydrocarbon molecules at high temperatures (e.g., 400° C. or more), leading to cracking of the molecules. In hydrocracking, hydrogen is added to bitumen molecules, which are then cracked over a catalyst system (e.g., platinum).

In a second stage, the cracked bitumen molecules are hydrotreated. In general, hydrotreating includes heating the cracked bitumen molecules in a hydrogen atmosphere to remove metals, nitrogen (e.g., as ammonia), and sulfur (e.g., as elemental sulfur).

The overall bitumen processing procedure typically produces approximately one barrel of synthetic crude oil for every 2.5 tons of oil sand material processed. Moreover, an energy equivalent of approximately one barrel of oil is used to produce three barrels of synthetic crude oil from oil sand-derived bitumen sources.

As another example, oil shale typically includes fine-grained sedimentary rock that includes significant amounts of kerogen (a mixture of various organic compounds in solid form). By heating oil shale, a vapor is liberated which can be purified to yield a hydrocarbon rich shale oil and a combustible hydrocarbon shale gas. Typically, the oil shale is heated to between 250° C. and 550° C. in the absence of oxygen to liberate the vapor.

The efficiency and cost-effectiveness with which usable hydrocarbon products can be extracted from oil sands material, oil shale, crude oil, and other oil-based raw materials can be improved by applying the methods disclosed herein. In addition, a variety of different hydrocarbon products (including various hydrocarbon fractions that are present in the raw material, and other types of hydrocarbons that are formed during processing) can be extracted from the raw materials.

In certain embodiments, in addition to Fenton oxidation, other methods can also be used to process raw and/or intermediate hydrocarbon-containing materials. For example, electron beams or ion beams can be used to process the materials. For example, ion beams that include one or more different types of ions (e.g., protons, carbon ions, oxygen ions, hydride ions) can be used to process raw materials. The ion beams can include positive ions and/or negative ions, in doses that vary from 1 Mrad to 2500 Mrad or more, e.g., 50, 100, 250, 350, 500, 1000, 1500, 2000, or 2500 MRad, or even higher levels.

Other additional processing methods can be used, including oxidation, pyrolysis, and sonication. In general, process parameters for each of these techniques when treating hydrocarbon-based raw and/or intermediate materials can be the same as those disclosed above in connection with biomass materials. Various combinations of these techniques can also be used to process raw or intermediate materials.

Generally, the various techniques can be used in any order, and any number of times, to treat raw and/or intermediate materials. For example, to process bitumen from oil sands, one or more of the techniques disclosed herein can be used prior to any mechanical breakdown steps, following one or more mechanical breakdown steps, prior to cracking, after cracking and/or prior to hydrotreatment, and after hydrotreatment. As another example, to process oil shale, one or more of the techniques disclosed herein can be used prior to either or both of the vaporization and purification steps discussed above. Products derived from the hydrocarbon-based raw materials can be treated again with any combination of techniques prior to transporting the products out of the processing facility (e.g., either via motorized transport, or via pipeline).

The techniques disclosed herein can be applied to process raw and/or intermediate material in dry form, in a solution or slurry, or in gaseous form (e.g., to process hydrocarbon vapors at elevated temperature). The solubility of raw or intermediate products in solutions and slurries can be controlled through selective addition of one or more agents such as acids, bases, oxidizing agents, reducing agents, and salts. In general, the methods disclosed herein can be used to initiate and/or sustain the reaction of raw and/or intermediate hydrocarbon-containing materials, extraction of intermediate materials from raw materials (e.g., extraction of hydrocarbon components from other solid or liquid components), distribution of raw and/or intermediate materials, and separation of intermediate materials from raw materials (e.g., separation of hydrocarbon-containing components from other solid matrix components to increase the concentration and/or purity and/or homogeneity of the hydrocarbon components).

In addition, microorganisms can be used for processing raw or intermediate materials, either prior to or following the use of the methods described herein. Suitable microorganisms include various types of bacteria, yeasts, and mixtures thereof, as disclosed previously. The processing facility can be equipped to remove harmful byproducts that result from the processing of raw or intermediate materials, including gaseous products that are harmful to human operators, and chemical byproducts that are harmful to humans and/or various microorganisms.

In some embodiments, the use of one or more of the techniques disclosed herein results in a molecular weight reduction of one or more components of the raw or intermediate material that is processed. As a result, various lower weight hydrocarbon substances can be produced from one or more higher weight hydrocarbon substances. In certain embodiments, the use of one or more of the techniques disclosed herein results in an increase in molecular weight of one or more components of the raw or intermediate material that is processed. For example, the various techniques disclosed herein can induce bond-formation between molecules of the components, leading to the formation of increased quantities of certain products, and even to new, higher molecular weight products. In addition to hydrocarbon products, various other compounds can be extracted from the raw materials, including nitrogen based compounds (e.g., ammonia), sulfur-based compounds, and silicates and other silicon-based compounds. In certain embodiments, one or more products extracted from the raw materials can be combusted to generate process heat for heating water, raw or intermediate materials, generating electrical power, or for other applications.

Processing oil sand materials (including bitumen) using one or more of the techniques disclosed herein can lead to more efficient cracking and/or hydrotreatment of the bitumen. As another example, processing oil shale can lead to more efficient extraction of various products, including shale oil and/or shale gas, from the oil shale. In certain embodiments, steps such as cracking or vaporization may not even be necessary if the techniques disclosed herein are first used to treat the raw material. Further, in some embodiments, by treating raw and/or intermediate materials, the products can be made more soluble in certain solvents, in preparation for subsequent processing steps in solution (e.g., steam blasting, sonication). Improving the solubility of the products can improve the efficiency of subsequent solution-based treatment steps. By improving the efficiency of other processing steps (e.g., cracking and/or hydrotreatment of bitumen, vaporization of oil shale), the overall energy consumed in processing the raw materials can be reduced, making extraction and processing of the raw materials economically feasible.

Accordingly, other embodiments are within the scope of the following claims.

What is claimed is:

1. A method of enhancing oxidative molecular weight reduction in cellulosic or lignocellulosic materials, the method comprising:
providing a mixture comprising a first cellulosic or lignocellulosic material having been exposed to ionizing radiation by a beam of particles comprising oxygen ions, one or more oxidants comprising ozone generated in-situ by the beam of particles, and one or more compounds comprising one or more naturally-occurring, non-radioactive group 5, 6, 7, 8, 9, 10 or 11 elements, the first cellulosic or lignocellulosic material having a first molecular weight; and
maintaining conditions effective to allow the one or more naturally-occurring, non-radioactive group 5, 6, 7, 8, 9, 10 or 11 elements to participate in a Fenton-type reaction, wherein hydroxyl radicals generated in the Fenton-type reaction then react with the first cellulosic or lignocellulosic material to produce a second cellulosic or lignocellulosic material having a second molecular weight lower than the first molecular weight.

2. The method of claim 1, wherein the one or more elements are in a 1+, 2+, 3+, 4+ or 5+ oxidation state.

3. The method of claim 1, wherein the one or more elements comprise Mn, Fe, Co, Ni, Cu or Zn.

4. The method of claim 1, wherein the one or more elements comprise Fe in the 2+, 3+ or 4+ oxidation state.

5. The method of claim 1, wherein the one or more oxidants are capable of increasing an oxidation state of at least some of said elements.

6. The method of claim 5, wherein the oxidant further comprises hydrogen peroxide.

7. The method of claim 1, wherein maintaining conditions effective to allow the elements to participate in a Fenton-type reaction comprises maintaining pH at or below about 5.5 during contact.

8. The method of claim 1, wherein providing a mixture comprises dispersing the first cellulosic or lignocellulosic material in water or an aqueous medium, and then adding first the one or more compounds and then the one or more oxidants.

9. The method of claim 1, wherein providing a mixture comprises dispersing the first cellulosic or lignocellulosic material in water or an aqueous medium, and then adding first the one or more oxidants and then the one or more compounds.

10. The method of claim 1, wherein a total maximum concentration of the elements in the one or more compounds measured in the mixture is from about 10 $\mu$M to about 500 mM.

11. The method of claim 1, wherein a total maximum concentration of the one or more oxidants is from about 100 $\mu$M to about 1 M.

12. The method of claim 1, wherein the one or more oxidants are applied to the mixture by irradiating the first cellulosic or lignocellulosic and the one or more compounds through air with the beam of particles, the beam of particles generating the one or more oxidants.

13. The method of claim 1, wherein the beam of particles further comprises one or more of: helium nuclei, argon ions, silicon ions, neon ions, carbon ions, phosphorus ions, and nitrogen ions.

14. The method of claim 1, wherein the mole ratio of the one or more elements to the one or more oxidants is from about 1:1000 to about 1:25.

15. The method of claim 1, wherein the mixture further includes one or more hydroquinones and/or one or more benzoquinones.

16. The method of claim 1, wherein the one or more oxidants are electrochemically or electromagnetically generated in-situ.

17. The method of claim 1, wherein the method further comprises contacting the second cellulosic or lignocellulosic material with an enzyme and/or microorganism.

18. The method of claim 1, wherein the method further comprises saccharifying the second cellulosic or lignocellulosic material and then fermenting the saccharified material.

* * * * *